United States Patent
Soferman et al.

(10) Patent No.: US 6,575,907 B1
(45) Date of Patent: Jun. 10, 2003

(54) DETERMINATION OF FETAL WEIGHT IN UTERO

(75) Inventors: Ziv Soferman, Givatayim (IL); Michael Berman, Har Adar (IL)

(73) Assignee: Biomedicom, Creative Biomedical Computing Ltd., Malha (IL)

( * ) Notice: Subject to any disclaimer, the term of this patent is extended or adjusted under 35 U.S.C. 154(b) by 0 days.

(21) Appl. No.: 09/351,252

(22) Filed: Jul. 12, 1999

(51) Int. Cl.[7] .................................................. A61B 8/00
(52) U.S. Cl. ......................... 600/438; 600/443; 128/916
(58) Field of Search .................................. 600/437, 438, 600/440, 441, 443, 447, 449; 73/625, 626, 618; 395/119

(56) References Cited

U.S. PATENT DOCUMENTS

| | | | |
|---|---|---|---|
| 4,341,120 A | * 7/1982 | Anderson | 73/618 |
| 5,239,591 A | 8/1993 | Ranganath | 382/6 |
| 5,588,435 A | 12/1996 | Weng et al. | |
| 5,605,155 A | 2/1997 | Chalana et al. | |
| 5,608,849 A | * 3/1997 | King, Jr. | 395/119 |
| 5,655,535 A | 8/1997 | Friemel et al. | |
| 5,795,296 A | 8/1998 | Pathak et al. | |

OTHER PUBLICATIONS

Product details—InViVo–ScanNT; Fraunhofer Institut fuer Graphische Datenverarbeitung IGD; Darmstadt, Germany.
Product details—3–D Ultrasound—Acquisition Methods Details, Life Imaging Systems Inc., London, Ontario, Canada.
"USCD Radiologists are Working on a New Ultrasound Technology that's Guaranteed to Produce Much Clearer Images in Three Dimensions", K. Deely; USCD Perspectives, Spring 1999.
Product details—Imaging software available from A1 Alpha Space Inc; Laguna Hills, CA, USA.
Product details—HDI1500, commercially available from Advanced Technology Laboratories; Bothell, WA, USA.
Product details—Voluson 530D, commercially available from Medison America; Pleasanton, CA, USA.
Product details—L3–Di, commercially available from Life Imaging Systems; London, Ontario, Canada.
Product details—EchoScan, Echo–View and Compact 3–D commercially avaiable from TomTec Imaging Systems; GmbH, Unterschleissheim, Germany.
Product details—NetralVUS, commercially available from ScImage Inc.; Los Altos, CA 94022, USA.
Product details—3–Scape, commercially available from Siemens AG; Erlangen, Germany.
Product details—Vitrea, commercially available from Vital Images Inc.; Minneapolis, MN, USA.

(List continued on next page.)

*Primary Examiner*—Marvin M. Lateef
*Assistant Examiner*—Ali M. Imam

(57) ABSTRACT

This invention discloses an apparatus for measuring the weight of a fetus in utero including an ultrasonic imager providing at least one ultrasonic image, a volume determiner operative to employ the at least one ultrasonic image to provide volume information relating to at least part of the volume of the fetus in utero, and a weight determiner operative to employ said volume information relating to at least part of the volume of the fetus and density information relating to the at least part of the volume of the fetus for providing an output indication representing the weight of the fetus in utero. A method for measuring the weight of a fetus in is also disclosed.

30 Claims, 26 Drawing Sheets

OTHER PUBLICATIONS

Product details—VoxarLib, commercially available from Voxar, Ldt.; Edinburgh, UK.

Product details—Logic 700 MR, commerically available from GE Ultrasound.

"On Active Contour Models and Balloons", L.D. Cohen, CVGIP: Image Understanding, vol. 53, No. 2, pp. 211–218 (1991).

"Finite–Element Methods for Active Contour Models and Balloons for 2–D and 3–D Images", L.D. Cohen and I. Cohen, IEEE Transactions on Pattern Analysis and Machine Intelligence, vol. 5 15, No. 11 (1993).

"Snakes, Active Contours, and Deformable Models", http://www.wpi.edu/~dima/ummed/presentation/index.html.

Thompson et al., "Estimation of Volume and Weight of the Perinate: Relationship to Morphometric Measurement by Ultrasonography", J Ultrasound Med 2:113–116. Mar. 1983.*

Liang et al., "Predicting birth weight by fetal upper–arm volume with use of three–dimensional ultrasonography", Am. J. Obstet Gynecol, vol. 177:632–8. Sep. 1997.*

Dudley et al., "A new method for fetal weight estimation using real–time ultrasound", British Journal of Obstetrics and Gynaecology, vol. 94, pp. 11–114. Feb. 1987.*

Shinozuka et al., "Fetal weight estimation by ultrasound measurement", Am. J. Obstet Gynecol, vol. 157:11405, 1987.*

* cited by examiner

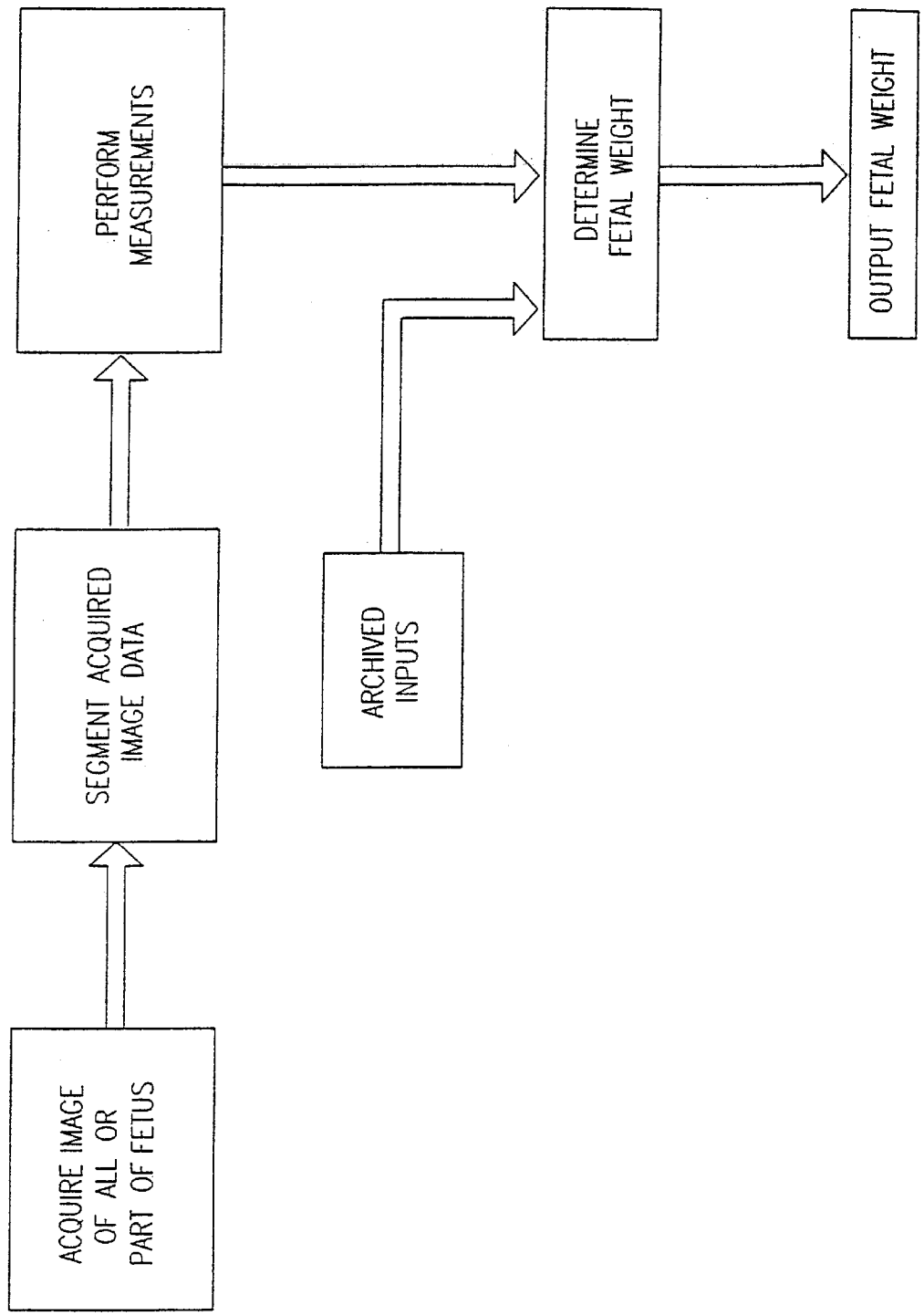

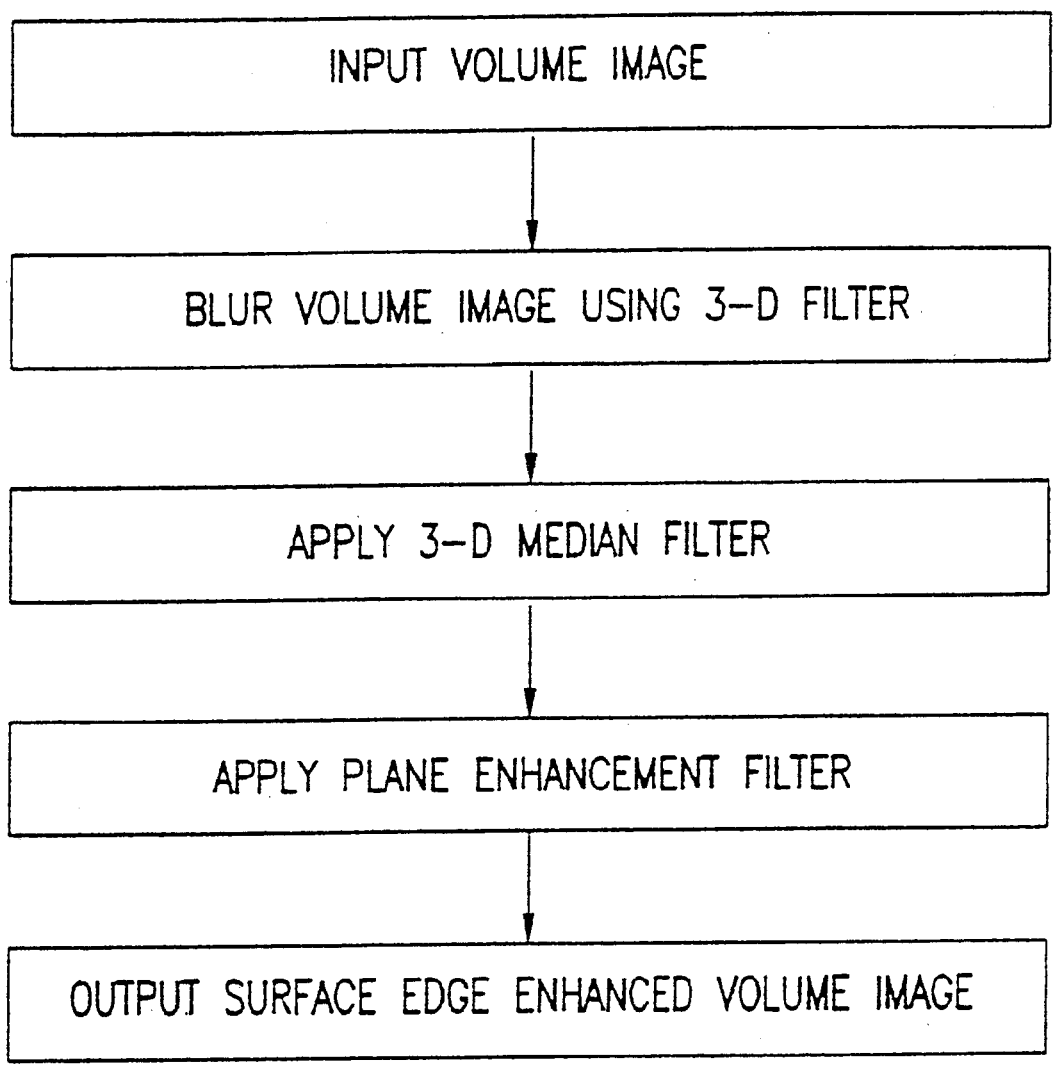

DEFINE $\phi, \theta$ AS THE ORIENTATION OF THE FILTERING OPERATOR AXIS RELATIVE TO THE VOLUME IMAGE SYSTEM OF AXES: LET $\phi$ BE THE ELEVATION ANGLE OF THE AXIS RELATIVE TO THE XY PLANE, AND $\theta$ THE ANGLE BETWEEN THE PROJECTED OPERATOR AXIS ON THE XY PLANE AND THE X DIRECTION. DISCRETIZE THE OPERATOR ORIENTATION ANGLES SO THAT:

$$\theta = k\Delta\theta, \Delta\theta = \pi/K, k = 0,1,2,3,...K-1; \phi = s\Delta\phi, \Delta\phi = \pi/2S, s = 0,1,2,3,...S$$

(TYPICALLY K=36, S=9).

DEFINE:

FOR EACH VOXEL POSITIONED AT $\underline{X}_0=(x_0,y_0,z_0)$ (IN THE VOLUME IMAGE COORDINATES) IN THE REGION OF INTEREST, CALCULATE THE DISCRETE CONVOLUTION/CORRELATION WITH THE ENHANCEMENT OPERATOR IN THE FOLLOWING WAY:

DEFINE X,Y,Z AS THE AXES OF THE VOLUMETRIC IMAGE COORDINATE SYSTEM.. DEFINE $\underline{I},\underline{J},\underline{K}$ TO BE 3 UNIT VECTORS IN THE MAIN DIRECTIONS IN THE OPERATOR'S SYSTEM OF AXES, AS SEEN IN FIG. 10: $\underline{K}$ IS A UNIT VECTOR ALONG THE OPERATOR'S SYMMETRY AXIS, $\underline{I}$ IS ORTHOGONAL TO $\underline{K}$ AND IS PARALLEL TO THE XY PLANE. (IF $\underline{K}$ IS PARALLEL TO THE Z DIRECTION OF THE VOLUME IMAGE SYSTEM- CHOOSE $\underline{I}$ TO BE ORTHOGONAL TO $\underline{K}$ AND TO THE X AXIS). CHOOSE $\underline{J}$ TO BE ORTHOGONAL BOTH TO $\underline{K}$ AND TO $\underline{I}$. MORE SPECIFICALLY, THE UNIT VECTORS IN TERMS OF THE X,Y,Z COORDINATE SYSTEM:

$\underline{K}=(cos(\phi)cos(\theta), cos(\phi)sin(\theta), sin(\phi))$
$\underline{I}=(sin(\theta),-cos(\theta),0)$
$\underline{J}=(-sin(\phi)cos(\theta), -sin(\phi)sin(\theta), cos(\phi))$ DEFINE $\underline{X}_0=(x_0,y_0,z_0)$ TO BE THE POSITION VECTOR OF THE OPERATOR'S CENTER IN THE X,Y,Z SYSTEM OF COORDINATES (CENTERED AT THE VOXEL OF THE SAME COORDINATES). A POINT WHOSE COORDINATES ARE (i,j,k) IN THE OPERATOR SYSTEM OF AXES, HAS THE COORDINATES
$\underline{X}(i,j,k)=\underline{X}_0+i\underline{I}+j\underline{J}+K\underline{k}$ (IN VECTOR NOTATION) IN THE X,Y,Z SYSTEM OF AXES.

DEFINE THE AVERAGE $\alpha$ OF THE IMAGE WITHIN A FILLED CIRCLE OF RADIUS R CENTERED AT $\underline{X}_0$ AND PERPENDICULAR TO THE OPERATOR AXIS AS FOLLOWS:

$$a(\underline{X}_0,\phi,\theta,R) = \frac{1}{Ninside} \sum_{i,j \in C} Vol\_Image[\underline{X}(i,j,0)]$$

WHERE: $C$ IS THE SET OF ALL (i,j) SUCH THAT $i^2+j^2 \leq R^2$, $Ninside$ IS THE NUMBER OF SUCH (i,j)'s WITHIN $C$, AND Vol_Image[$\underline{X}$(i,j,0)] IS THE VALUE OF THE VOXEL POSITIONED AT $\underline{X}$(i,j,0) IN THE VOLUME IMAGE SYSTEM OF AXES.

FIG. 9A

FOR EACH VOXEL IN THE REGION OF INTEREST USE THE ABOVE AVERAGE TO PRODUCE THE DIRECTIONAL DERIVATIVE $h'$ BY SUBTRACTING FROM THE AVERAGE '$a$' WITHIN A FILLED CIRCLE CENTERED AT THAT VOXEL, HALF OF THE AVERAGES WITHIN PARALLEL CIRCLES, NAMELY CALCULATE:

$$h'(\underline{X}_0, \phi, \theta, R, D) = \alpha(\underline{X}_0, \phi, \theta, R) - 0.5(\alpha(\underline{X}_1, \phi, \theta, R) + \alpha(\underline{X}_2, \phi, \theta, R))$$

WHERE: $\underline{X}_0$ IS THE POSITION VECTOR OF THE VOXEL, $\underline{X}_1 = \underline{X}_0 + D\underline{K}$; $\underline{X}_2 = \underline{X}_0 - D\underline{K}$ AND $D$ IS THE DISTANCE BETWEEN THE CENTRAL CIRCLE AND THE TWO PARALLEL ONES.

IN PRACTICE $\alpha(\underline{X}_1, \phi, \theta, R)$ AND $\alpha(\underline{X}_2, \phi, \theta, R)$ ARE OBTAINED BY BILINEAR INTERPOLATION FROM THE VALUES OF THE AVERAGE $a$ AT NEIGHBORING INTEGER COORDINATES.

---

FOR EACH VOXEL IN THE REGION OF INTEREST FIND THE MAXIMAL VALUE OF $-h'(\underline{X}_0, s \cdot \Delta\phi, k \cdot \Delta\theta, R, D)$ OVER ALL $k=0,1,2,...K-1$; $s=0,1,2,...,S$ AND
$\Delta\theta = \pi/K$ ; $\Delta\phi = \pi/2S$ (TYPICALLY K=36 AND S=9).
IF THE MAXIMUM ASSOCIATED WITH A CERTAIN VOXEL IS LOWER THAN ZERO THEN SET IT TO ZERO. NAMELY, $$h(\underline{X}_0, R, D) = MAX\{0, \underset{\substack{0 \leq k \leq K-1 \\ 0 \leq s \leq S}}{MAX}\{-h'(\underline{X}_0, s \cdot \Delta\phi, k \cdot \Delta\theta, R, D)\}\}$$

---

DEFINE THE SURFACE-EDGE ENHANCED IMAGE CORRESPONDING TO THE GIVEN IMAGE TO BE A VOLUME IMAGE WHOSE VALUE AT THE VOXEL POSITIONED AT $\underline{X}_0 = (x_0, y_0, z_0)$ IS $h(\underline{X}_0, R, D)$ WHERE THE OPERATOR $h$ IS APPLIED TO THE GIVEN IMAGE, FOR $\underline{X}_0$ WITHIN THE REGION OF INTEREST, AND ZERO FOR $\underline{X}_0$ OUTSIDE THE REGION OF INTEREST.

---

OBTAIN SURFACE-EDGE ENHANCED IMAGE

FIG. 9B

FOR EACH ORIENTATION $\theta$ RELATIVE TO THE HORIZONTAL AXIS (X) OF THE IMAGE WHERE: $\theta = k\Delta\theta, \Delta\theta = \pi/K$, $k = 0,1,2,3,...K-1$, (TYPICALLY K=36) DEFINE:

FOR EACH PIXEL IN THE REGION OF INTEREST CALCULATE THE DISCRETE AVERAGE 'a' ALONG A LINE OF LENGTH L ORIENTED AT AN ANGLE $\theta$ AND CENTERED AT THE PIXEL WITH INTEGER COORDINATES (x0,y0) AS SEEN IN FIG. 17 IN THE FOLLOWING WAY:

$$a(x0, y0, \theta, L) = \frac{1}{N+1} \sum_{m=-N/2}^{+N/2} \text{Image}(x0 + m\Delta x, y0 + m\Delta y)$$

where $$\Delta x = \frac{L}{N}\cos(\theta); \Delta y = \frac{L}{N}\sin(\theta)$$

L IS THE LENGTH OF THE LINE IN PIXELS, N+1 IS THE NUMBER OF SAMPLING POINTS ALONG THE LINE. N HAS TO BE AN EVEN NUMBER, TYPICALLY LARGER THAN 2L. Image$(x0 + m\Delta x, y0 + m\Delta y)$ IS THE IMAGE VALUE AT $(x0 + m\Delta x, y0 + m\Delta y)$. IF THE COORDINATES $(x0 + m\Delta x, y0 + m\Delta y)$ ARE NON-INTEGERS, THE IMAGE VALUE AT $(x0 + m\Delta x, y0 + m\Delta y)$ IS OBTAINED BY BILINEAR INTERPOLATION FROM THE IMAGE VALUES AT NEIGHBORING PIXELS WITH INTEGER COORDINATES.

---

FOR EACH PIXEL IN THE REGION OF INTEREST USE THE ABOVE AVERAGE TO PRODUCE THE DIRECTIONAL DERIVATIVE $h'$ BY SUBTRACTING FROM THE AVERAGE 'a' ALONG THE LINE CENTERED AT THE PIXEL, HALF OF THE AVERAGES ALONG PARALLEL LINES, NAMELY CALCULATE:

$$h'(x0, y0, \theta, D, L) = a(x0, y0, \theta, L) - 0.5 \cdot (a(x1, y1, \theta, L) + a(x2, y2, \theta, L))$$

where:

$$x1 = x0 + D \cdot COS(\theta + \pi/2); y1 = y0 + D \cdot SIN(\theta + \pi/2)$$
$$x2 = x0 + D \cdot COS(\theta - \pi/2); y2 = y0 + D \cdot SIN(\theta - \pi/2)$$

IN WHICH D IS THE DISTANCE BETWEEN THE CENTRAL LINE AND THE TWO PARALLEL SIDE LINES.

IN PRACTICE $a(x1, y1, \theta, L), a(x2, y2, \theta, L))$ ARE OBTAINED BY BILINEAR INTERPOLATION FROM THE VALUES OF THE AVERAGE $a(i, j, \theta, L)$ AT NEIGHBORING INTEGER COORDINATES.

FIG. 13A

FOR EACH PIXEL IN THE REGION OF INTEREST FIND THE MAXIMAL VALUE OF $-h'(x0, y0, k \cdot \Delta\theta, D, L)$ FOR $k$=0,1,2,...,K-1, AND $\Delta\theta = \pi/K$. TYPICALLY K=36. IF THE MAXIMUM ASSOCIATED WITH A CERTAIN PIXEL IS LOWER THAN ZERO THEN SET IT TO ZERO. NAMELY, $$h(x0, y0, D, L) \stackrel{def}{=} MAX\{0, \underset{0 \leq k \leq K-1}{MAX}\{-h'(x0, y0, k \cdot \Delta\theta, D, L)\}\}$$

DEFINE THE EDGE ENHANCED IMAGE AT THE PIXEL (x0,y0) TO BE THE VALUE OF $h(x0,y0,D,L)$ FOR (x0,y0) IN THE REGION OF INTEREST, AND ZERO ELSEWHERE. THE RESULT IS A NEW IMAGE WHICH IS THE EDGE ENHANCED IMAGE. THE PARAMETERS D AND L ARE OPTIMIZED THROUGH EXPERIENCE.

OUTPUT EDGE ENHANCED IMAGE

FIG. 13B

AS SEEN IN FIG. 18B, TO EACH SUCH CONNECTING SEGMENT ASSOCIATE A WEIGHT ACCORDING TO: (1) ITS PROXIMITY TO THE INITIAL MARKING (2) THE DEGREE OF SIMILARITY OF THE CONNECTING SEGMENT DIRECTION TO THE CORRESPONDING DIRECTION OF THE INITIAL MARKINGS AT THAT LOCATION, (3) THE AVERAGE INTENSITY OF THE EDGE ENHANCED IMAGE ALONG THE CONNECTING SEGMENT, AND (4) OPTIONALLY INTRODUCE AN INPUT WEIGHT FROM PREVIOUS OR OTHER SLICE/S.. AN EXAMPLE OF THE FORMULA USED IN THE PREFERRED EMBODIMENT:

DEFINE THE WEIGHTING FUNCTIONS $W_{ij}^{t}$ TO BE THE WEIGHT ASSOCIATED WITH THE SEGMENT CONNECTING DISCRETIZATION POINT $i$ IN NORMAL $t$ TO DISCRETIZATION POINT $j$ IN NORMAL $t+1$.

$$W_{ij}^{t} = -\alpha W_{1ij}^{t} + \beta W_{2ij}^{t} + \gamma W_{3ij}^{t} + \delta W_{4ij}^{t}$$

WHERE:

$W_{1ij}^{t}$ = AVERAGE OF VALUES IN THE ARRAY h(i,j,D,L) (THE EDGE ENHANCED IMAGE ARRAY) ALONG THE CONNECTING SEGMENT FROM POINT i ON NORMAL t TO POINT j ON NORMAL t+1. $\alpha, \beta, \gamma, \delta$ ARE WEIGHTING FACTORS OPTIMIZED THROUGH EXPERIENCE.

IN THIS SPECIFIC EXAMPLE, ALL NORMALS ARE DISCRETIZED INTO 2U+1 EQUALLY SPACED POINTS. $-U \leq i \leq U$; $-U \leq j \leq U$ AND THE NORMAL INTERSECTS THE INITIAL MARKING FOR i=j=0 AND ALL NORMALS ARE OF THE SAME LENGTH.

$W_{2ij}^{t}$ = |i-j|/2U APPROXIMATING THE DEGREE OF SIMILARITY OF THE DIRECTION OF THE CONNECTING SEGMENT TO THE CORRESPONDING DIRECTION OF THE INITIAL MARKING AT THAT LOCATION.

$W_{3ij}^{t}$ = (i+j)/2U THE PROXIMITY OF THE CONNECTING SEGMENT TO THE INITIAL MARKING.

$W_{4ij}^{t}$ = OPTIONAL: INPUT WEIGHT TERM FROM OTHER SLICE/S

FIG. 14B

DETERMINATION OF FETAL WEIGHT IN UTERO

FIELD OF THE INVENTION

The present invention relates to fetal weight determination generally and more particularly to fetal weight determination based on ultrasonic imaging.

BACKGROUND OF THE INVENTION

The following publications describe prior art existing fetal imaging apparatus, and methods for measuring fetal weight:

"Sonographic Estimation of Fetal Weight", Frank P. Hadlock et al., Radiology 1984, Vol. 150, pp. 535–540; and the references cited therein;

"Obstetric Ultrasound", Website: http://www.ob-ultrasound.net, references and links therefrom;

Website: http://www.shinozuka.com/US;

"American Institute of Ultrasound in Medicine", Website: http://www.aium.org.

Various techniques are known for fetal imaging in utero using ultrasonic technology.

Conventional systems which provide fetal imaging in utero are known inter alia from the following publications:

U.S. Pat. No. 5,239,591;

InViVo-ScanNT of the Fraunhofer Institut fuer Graphische Datenverarbeitung IGD in Darmstadt, Germany, commercially available;

3-D Ultrasound—Acquisition Methods Details, of Life Imaging Systems, Inc. of London, Ontario UCSD radiologists are working on a new ultrasound technology that's guaranteed to produce much clearer images in three dimensions, by Kate Deely, UCSD Perspectives, Spring 1999;

Product literature relating to the following products:

Imaging software available from A1 Alpha Space, Inc, of Laguna Hills, Calif., U.S.A. and from Echotech 3-D of Hallbergmoos, Germany;

HDI1500 commercially available from ATL—Advanced Technology Laboratories, Bothell, Wash., U.S.A.;

Voluson 530D commercially available from Kretztechnik AG of Zipf, Austria and from Medison America of Pleasanton, Calif., U.S.A. This ultrasound system includes a scalpel feature which enables manual removal of occlusions blocking full visualization of a fetal face.

L3-Di commercially available from Life Imaging Systems Inc. of London, Ontario, Canada;

Echo-Scan, Echo-View and Compact3-D commercially available from TomTec Imaging Systems GmbH of Unterschleissheim, Germany;

NetralVUS, commercially available from ScImage, Inc. of Los Altos, Calif. 94022, U.S.A.;

3-Scape commercially available from Siemens AG of Erlangen, Germany;

Vitrea, commercially available from Vital Images, Inc of Minneapolis, Minn., U.S.A.;

VoxarLib, commercially available from Voxar Ltd. of Edinburgh, UK;

LOGIC 700 MR commercially available from GE Ultrasound.

SUMMARY OF THE INVENTION

The present invention seeks to provide an improved system for fetal weight determination in utero.

There is thus provided in accordance with a preferred embodiment of the present invention apparatus for measuring the weight of a fetus in utero including an ultrasonic imager providing at least one ultrasonic image, a volume determiner operative to employ at least one ultrasonic image to provide volume information relating to at least part of the volume of the fetus in utero, and a weight determiner operative to employ the volume information relating to at least part of the volume of the fetus and density information relating to at least part of the volume of the fetus for providing an output indication representing the weight of the fetus in utero.

Further in accordance with a preferred embodiment of the present invention the at least one of the volume determiner and the weight determiner is operative to construct a generally full fetal body volume from incomplete volume information based on known correlation information.

Still further in accordance with a preferred embodiment of the present invention the volume determiner includes computerized image processing based segmenter operative to employ the at least one ultrasonic image to provide size information relating to at least part of the fetus in utero.

Preferably the volume determiner includes a computerized edge detection based segmenter.

Additionally in accordance with a preferred embodiment of the present invention the at least one of the imager and the volume determiner operates on a slice-by-slice basis.

Further in accordance with a preferred embodiment of the present invention the volume determiner also includes a measurement tool which provides information relating to at least one of overall fetal volume, volumes of body parts of the fetus, areas of various cross sections of the fetus and sizes of various bones and body parts of the fetus.

Preferably the weight determiner includes a fetal weight calculator receiving inputs relating to at least one of measurement data derived from measurements of a multiplicity of other fetuses, correlations between the measurement data and birth weights, and data from earlier measurements of the same fetus.

Still further in accordance with a preferred embodiment of the present invention the measurement tool is operative to measure features of the fetus in at least one selected plane.

Additionally in accordance with a preferred embodiment of the present invention the volume determiner includes computerized image processing based segmenter operative to employ the at least one ultrasonic image to provide size information relating to at least part of the fetus in utero.

Moreover in accordance with a preferred embodiment of the present invention includes a fetal weight calculator receiving inputs relating to at least one of measurement data derived from measurements of a multiplicity of other fetuses, correlations between the measurement data and birth weights, and data from earlier measurements of the same fetus.

There is also provided in accordance with a preferred embodiment of the present invention apparatus including an ultrasonic imager providing at least one ultrasonic image, a computerized image processing based segmenter operative to employ the at least one ultrasonic image to provide size information relating to at least part of the fetus in utero, and a weight determiner operative to employ said size information for providing an output indication representing the weight of said fetus in utero.

Further in accordance with a preferred embodiment of the present invention at least one of the volume determiner and the weight determiner is operative to construct a generally full fetal body volume from incomplete volume information based on known correlation information.

Preferably the volume determiner includes a computerized edge detection based segmenter.

Additionally or alternatively at least one of the imager and the volume determiner operates on a slice-by-slice basis.

Still further in accordance with a preferred embodiment of the present invention the volume determiner also includes a measurement tool which provides information relating to at least one of overall fetal volume, volumes of body parts of the fetus, areas of various cross sections of the fetus and sizes of various bones and body parts of the fetus.

Additionally in accordance with a preferred embodiment of the present invention the weight determiner includes a fetal weight calculator receiving inputs relating to at least one of measurement data derived from measurements of a multiplicity of other fetuses, correlations between the measurement data and birth weights, and data from earlier measurements of said same fetus.

Still further in accordance with a preferred embodiment of the present invention the measurement tool is operative to measure features of the fetus in at least one selected plane.

Additionally in accordance with a preferred embodiment of the present invention the at least one of the volume determiner and the weight determiner is operative to construct a generally full fetal body volume from incomplete volume information based on known correlation information.

Further in accordance with a preferred embodiment of the present invention at least one of the imager and the volume determiner operates on a slice-by-slice basis.

Preferably the segmenter is fully automatic. Alternatively segmenter is semi-automatic.

Still further in accordance with a preferred embodiment of the present invention the segmenter operates substantially in real time.

Moreover in accordance with a preferred embodiment of the present invention the segmenter defines geometrical boundaries in at least one slice of the volume by employing previously acquired information relating to at least another slice of the volume. Preferably the segmenter defines geometrical boundaries in at least one slice of the volume by employing previously acquired information relating to at least another slice of the volume.

Additionally the segmenter operates in a slice-by-slice manner.

There is provided in accordance with yet another preferred embodiment of the present invention a method for measuring the weight of a fetus in utero, the method includes providing at least one ultrasonic image, employing the at least one ultrasonic image to provide volume information relating to at least part of the volume of the fetus in utero, and employing the volume information relating to at least part of the volume of the fetus and density information relating to the at least part of the volume of the fetus for providing an output indication representing the weight of the fetus in utero.

Further in accordance with a preferred embodiment of the present invention the method includes constructing a generally full fetal body volume from incomplete volume information based on known correlation information.

Still further in accordance with a preferred embodiment of the present invention the volume determiner comprises computerized image processing based segmenter operative to employ the at least one ultrasonic image to provide size information relating to at least part of the fetus in utero.

Additionally in accordance with a preferred embodiment of the present invention the step of employing the volume information comprises computerized edge detection.

Moreover in accordance with a preferred embodiment of the present invention and also including utilizing information relating to at least one of overall fetal volume, volumes of body parts of the fetus, areas of various cross sections of the fetus and sizes of various bones and body parts of the fetus.

Preferably the method also includes utilizing inputs relating to at least one of measurement data derived from measurements of a multiplicity of other fetuses, correlations between the measurement data and birth weights, and data from earlier measurements of the same fetus.

Further in accordance with a preferred embodiment of the present invention including measurement of features of the fetus in at least one selected plane.

Additionally in accordance with a preferred embodiment of the present invention including computerized image processing based segmentation which employs the at least one ultrasonic image to provide size information relating to at least part of the fetus in utero.

Preferably the method utilizes inputs relating to at least one of measurement data derived from measurements of a multiplicity of other fetuses, correlations between the measurement data and birth weights, and data from earlier measurements of the same fetus.

There is also provided in accordance with another preferred embodiment of the present invention a method for measuring the weight of a fetus in utero including the steps of providing at least one ultrasonic image, one ultrasonic image in computerized image processing based segmentation to provide size information relating to at least part of the fetus in utero, and employing the size information for providing an output indication representing the weight of the fetus in utero.

Further in accordance with a preferred embodiment of the present invention, the method includes constructing a generally full fetal body volume from incomplete volume information based on known correlation information.

Still further in accordance with a preferred embodiment of the present invention including computerized edge detection segmentation.

Preferably the segmentation operates on a slice-by-slice basis.

Additionally in accordance with a preferred embodiment of the present invention, the method includes providing information relating to at least one of overall fetal volume, volumes of body parts of the fetus, areas of various cross sections of the fetus and sizes of various bones and body parts of the fetus.

Preferably the method includes utilizing at least one of measurement data derived from measurements of a multiplicity of other fetuses, correlations between the measurement data and birth weights, and data from earlier measurements of the same fetus.

Moreover in accordance with a preferred embodiment of the present invention, the method includes measuring features of the fetus in at least one selected plane.

Further in accordance with a preferred embodiment of the present invention utilizing inputs relating to at least one of measurement data derived from measurements of a multiplicity of other fetuses, correlations between said measurement data and birth weights, and data from earlier measurements of the same fetus.

Additionally constructing a generally full fetal body volume from incomplete volume information based on known correlation information.

Preferably the imager employs ultrasound.

Preferably the segmentation operates fully automatically. Alternatively the segmentation operates semi-automatically.

Additionally in accordance with a preferred embodiment of the present invention the segmentation operates substantially in real time.

Still further in accordance with a preferred embodiment of the present invention the segmentation defines geometrical boundaries in at least one slice of the volume by employing previously acquired information relating to at least another slice of the volume.

Preferably the segmentation operates in a slice-by-slice manner.

In accordance with a preferred embodiment of the present invention the volume determiner and/or the weight determiner are operative to determine fetal weight from volumes and densities of various body components, such as bones, fat, muscle, skin, soft tissue and fluid.

BRIEF DESCRIPTION OF THE DRAWINGS

The present invention will be understood and appreciated more fully from the following detailed description, taken in conjunction with the drawings in which:

FIG. 2 is a simplified flow chart illustrating operation of the system of FIG. 1 in accordance with a preferred embodiment of the present invention;

FIG. 7 is a flow chart illustrating a surface edge enhancement step of the operation of FIG. 6 in accordance with a preferred embodiment of the present invention;

FIGS. 9A and 9B together are a flowchart illustrating a three-dimensional filtering operation performed in accordance with a preferred embodiment of the present invention on an original volume image;

FIGS. 13A and 13B together are a flowchart illustrating a two-dimensional filtering operation performed in accordance with a preferred embodiment of the present invention on an original volume image;

FIGS. 14A and 14B together are a flow chart illustrating one part of an optimal boundary defining step of the operation of FIG. 11 in accordance with a preferred embodiment of the present invention;

DETAILED DESCRIPTION OF PREFERRED EMBODIMENTS

Figure 1:
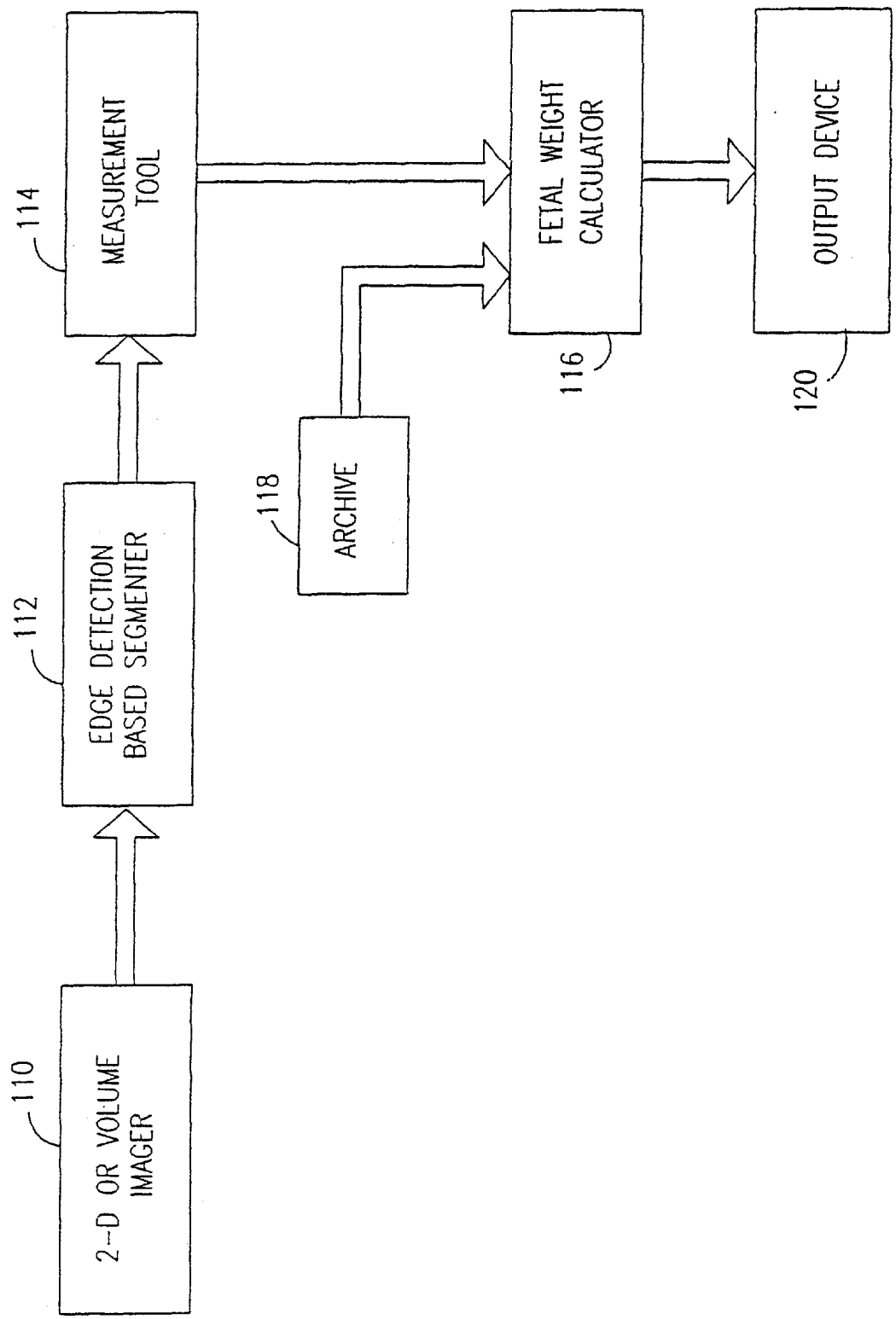
FIG. 1 is a simplified block diagram illustration of a fetal weight determination system constructed and operative in accordance with a preferred embodiment of the present invention and employing an imager and a segmenter.

Reference is now made to FIG. 1, which is a simplified block diagram illustration of a fetal weight determination system constructed and operative in accordance with a preferred embodiment of the present invention.

As seen in FIG. 1, the fetal weight determination system of an embodiment of the present invention preferably comprises a 2-D or a volume imager 110. Imager 110 may be of any suitable type and may employ any suitable technology, such as, for example, ultrasound imaging. It is also possible that magnetic resonance imaging (MRI) could be employed. Currently available ultrasound volume imagers and imaging software include:

Imaging software available from A1 Alpha Space, Inc, of Laguna Hills, Calif., U.S.A. and from Echotech 3-D of Hallbergmoos, Germany;

HDI1500 commercially available from ATL—Advanced Technology Laboratories, Bothell, Wash., U.S.A.;

Voluson 530D commercially available from Kretztechnik AG of Zipf, Austria and from Medison America of Pleasanton, Calif., U.S.A.

L3-Di commercially available from Life Imaging Systems Inc. of London, Ontario, Canada;

Echo-Scan, Echo-View and Compact3-D commercially available from TomTec Imaging Systems GmbH of Unterschleissheim, Germany;

NetralVUS, commercially available from ScImage, Inc. of Los Altos, Calif. 94022, U.S.A.;

3-Scape commercially available from Siemens AG of Erlangen, Germany;

Vitrea, commercially available from Vital Images, Inc of Minneapolis, Minn., U.S.A.;

VoxarLib, commercially available from Voxar Ltd. of Edinburgh, UK;

Conventional 2-D ultrasound images are also available from the following sources: ATL—Advanced Technology Laboratories, Bothell, Wash., U.S.A., Seimens AG, Acuson Corporation of Mountain View, Calif., U.S.A., GE Medical Systems of Milwaukee, Wis., U.S.A., Toshiba America Medical Systems of Tustin, Calif., U.S.A., Hewlett-Packard Medical Group of Palo Alto, Calif.

It is appreciated that most currently available volume imagers operate on a slice-by-slice basis. It is anticipated, however, that volume imagers which do not operate on a slice-by-slice basis will become available in the future and will also be useful in the present invention.

In accordance with a preferred embodiment of the present invention, image data from imager 110 is supplied to an image processing based computerized segmenter, preferably an edge detection based segmenter 112 preferably embodied in a workstation including a display and a suitable user input device (not shown). Typically segmenter 112 receives the output of imager 110 and enables a workstation operator, using that output, to readily locate and isolate a fetal image.

Segmenter 112, as will be described hereinbelow in detail, is operative in a computer-assisted manner, preferably under the control of the operator, to differentiate between various body parts and tissues and to distinguish the fetus from its environment, such as for example, from the amniotic fluid in which it resides and the surrounding placenta and uterus.

Preferably modified or annotated image data from segmenter 112 is employed by a measurement tool 114 to provide information relating to overall fetal volume, volumes of body parts of the fetus, areas of various cross sections of the fetus, sizes of various bones and body parts of the fetus.

This information is supplied to a fetal weight calculator 116, which may also receive inputs from an archive 118. Archive 118 may include information relating to at least one of measurement data derived from measurements of a multiplicity of other fetuses, correlations between said measurement data and birth weights, and data from earlier measurements of said same fetus and combinations of the foregoing.

The fetal weight calculator 116 is operative to employ inputs received from measurement tool 114 and archive 118 in one or more operational modes to produce an output indication of estimated fetal weight. The output indication is supplied to an output device 120, such as a computerized medical archive, local or remote display, printer, annunciator, recorder or a combination of the foregoing with any other functionality.

It is additionally appreciated that there may be cases where operator input in the operation of measurement tool 114 may be unnecessary. In such a case, the measurement tool 114 may be entirely computer controlled and operated.

It is appreciated that edge detection based segmenter 112 may be integrated in the same computer platform which serves to control the operation of imager 110.

Reference is now made to FIG. 2, which is a simplified flow chart illustrating operation of the system of FIG. 1 in accordance with a preferred embodiment of the present invention.

As seen in FIG. 2, the fetal weight determination methodology of an embodiment of the present invention preferably employs a 2-D or volume imager, preferably imager 110 (FIG. 1), to acquire an image of all or part of the fetus.

In accordance with a preferred embodiment of the present invention, the acquired image data is segmented by an edge detection based segmenter, preferably segmenter 112 (FIG. 1).

The segmentation functionality, as will be described hereinbelow in detail, is operative in a computer-assisted manner, preferably under the control of the operator, to differentiate between various body parts and tissues and to distinguish the fetus from its environment, such as for example, from the amniotic fluid in which it resides and the surrounding placenta and uterus.

The output of the segmenter is employed by a measurement tool, preferably measurement tool 114 (FIG. 1) to provide information relating to overall fetal volume and preferably also to provide information relating to volumes of body parts of the fetus, areas of various cross sections of the fetus, sizes of various bones and body parts of the fetus.

A fetal weight calculator, preferably fetal weight calculator 116 (FIG. 1) provides an estimate of fetal weight and employs for this purpose the measurements carried out by the measurement tool as well as preferably also archived inputs, such as, for example, information relating to at least one of measurement data derived from measurements of a multiplicity of other fetuses, correlations between said measurement data and birth weights, and data from earlier measurements of said same fetus.

Figure 3A:
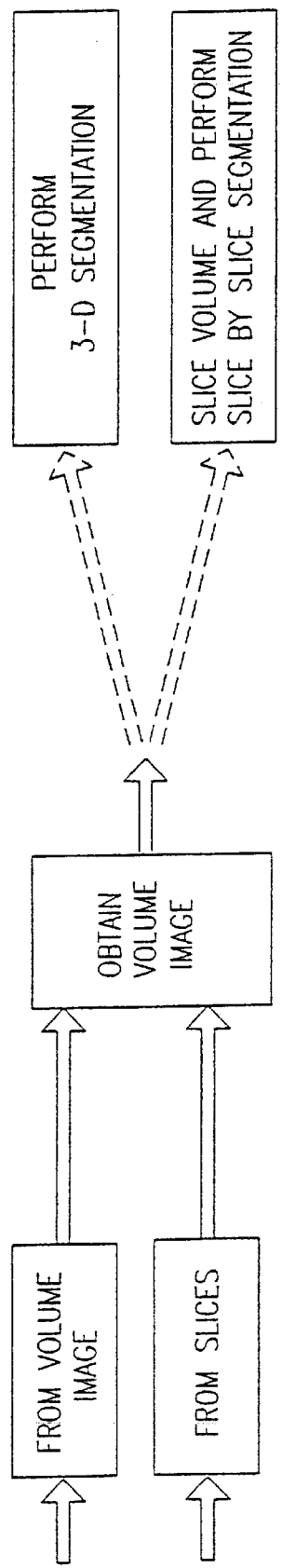
FIGS. 3A & 3B are flow charts each illustrating an alternative embodiment of an initial part of the operation shown in FIG. 2.
Figure 3B:
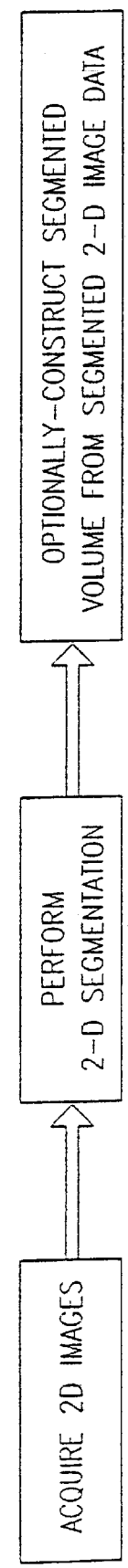

Reference is now made to FIGS. 3A & 3B, which are flow charts each illustrating an alternative embodiment of an initial part of the operation shown in FIG. 2 including image acquisition and segmentation.

As seen in FIG. 3A, a volume image of a fetus may be obtained either as a volume image directly from a volume imager or by construction from a multiplicity of slices produced by a 2-D imager. The volume image may be segmented either by 3-D segmentation or by slice-by-slice segmentation. In both cases segmented volume image data is provided.

FIG. 3B illustrates an alternative wherein 2-D images are acquired and 2-D segmentation is performed thereon, producing segmented 2-D image data. If desired, the segmented 2-D image data may be used to construct segmented volume image data.

Figure 4:
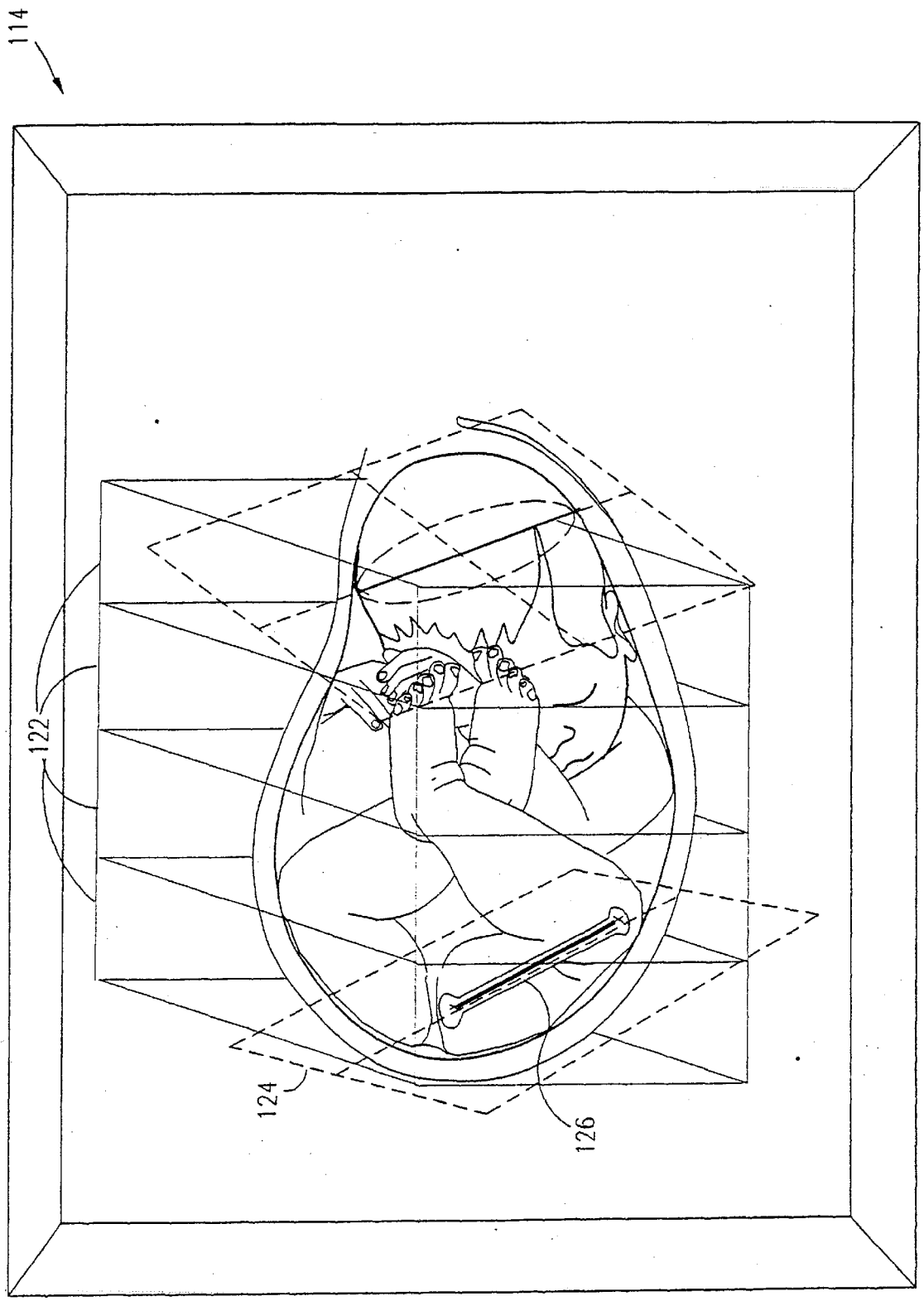
FIG. 4 is a partially pictorial illustration which assists in the understanding of a further part of the operation of FIG. 2.

Reference is now made to FIG. 4, which is a pictorial illustration showing some of the features of the measurement tool 114 (FIG. 1).

It is also seen that independently of the slices 122 which make up a volume image of the fetus, the measurement tool 114 is operative to measure features of the fetus along selected planes, such as plane 124. In this case, plane 124 is aligned with a femur 126 of the fetus, the length of which it is sought to measure.

Figure 5A:
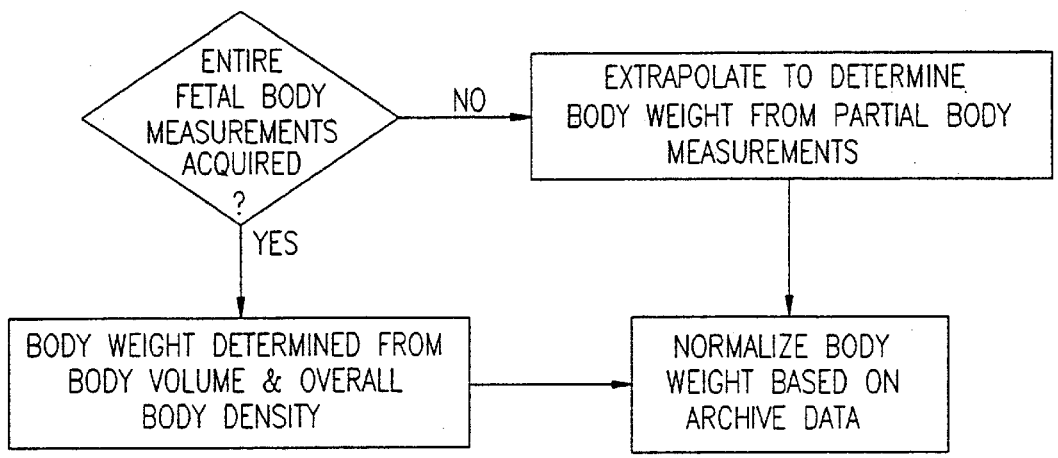
FIGS. 5A & 5B are flow charts each illustrating an alternative embodiment of a final part of the operation shown in FIG. 2.
Figure 5B:
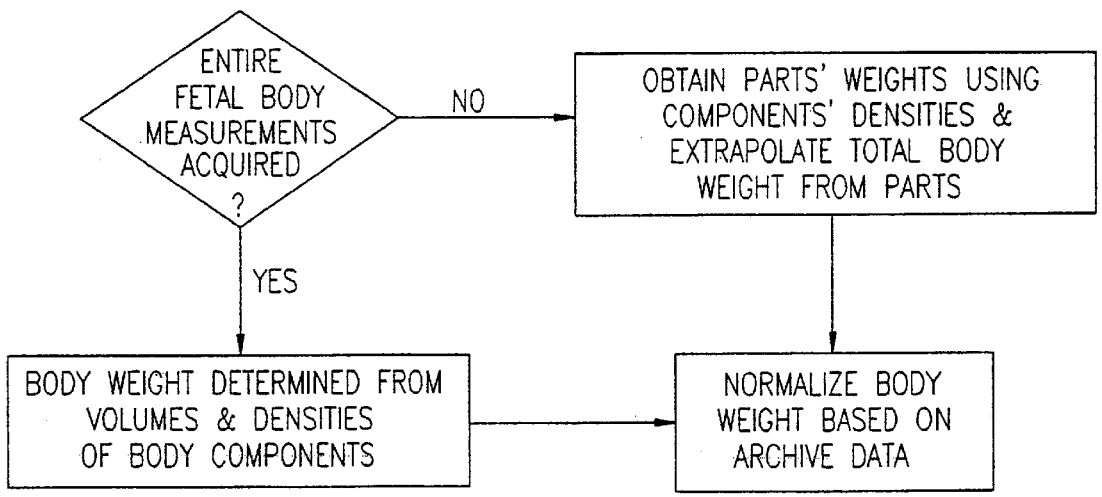

Reference is now made to FIGS. 5A & 5B, which are flow charts each illustrating an alternative embodiment of a final part of the operation shown in FIG. 2, including the fetal weight calculation.

As seen in FIG. 5A, the fetal weight calculation may be carried out based on measurements of the entire fetal body or only parts thereof. Where only parts of the fetal body are measured, such as only the torso and the head, suitable extrapolations may be carried out in order to enable a full body weight determination to be made. In such a case either a whole body density or densities of the measured parts of the fetal body may be used.

Optionally, statistically, theoretically or empirically derived or other archived correlation information may be used to normalize or otherwise modify the fetal weight determined as aforesaid. For example, known correlations between fetal weight and one or more of femur length, crown-rump length, abdominal circumference and biparietal diameter may be employed to normalize or modify the fetal weight determined from the measurements.

Referring now to FIG. 5B, it is seen that whereas in the functionality of FIG. 5A, the entire fetal body or body parts are treated as units having uniform density for the purposes of weight determination, in FIG. 5B, measurements of various components of the fetal body which have substantially different densities, such as tissue, bone and fluid, are utilized to provide separate weight determinations which are added to arrive at a total fetal body weight. Here, also statistically derived or other archived information may be used to normalize or otherwise modify the fetal weight determined as aforesaid.

Figure 6:
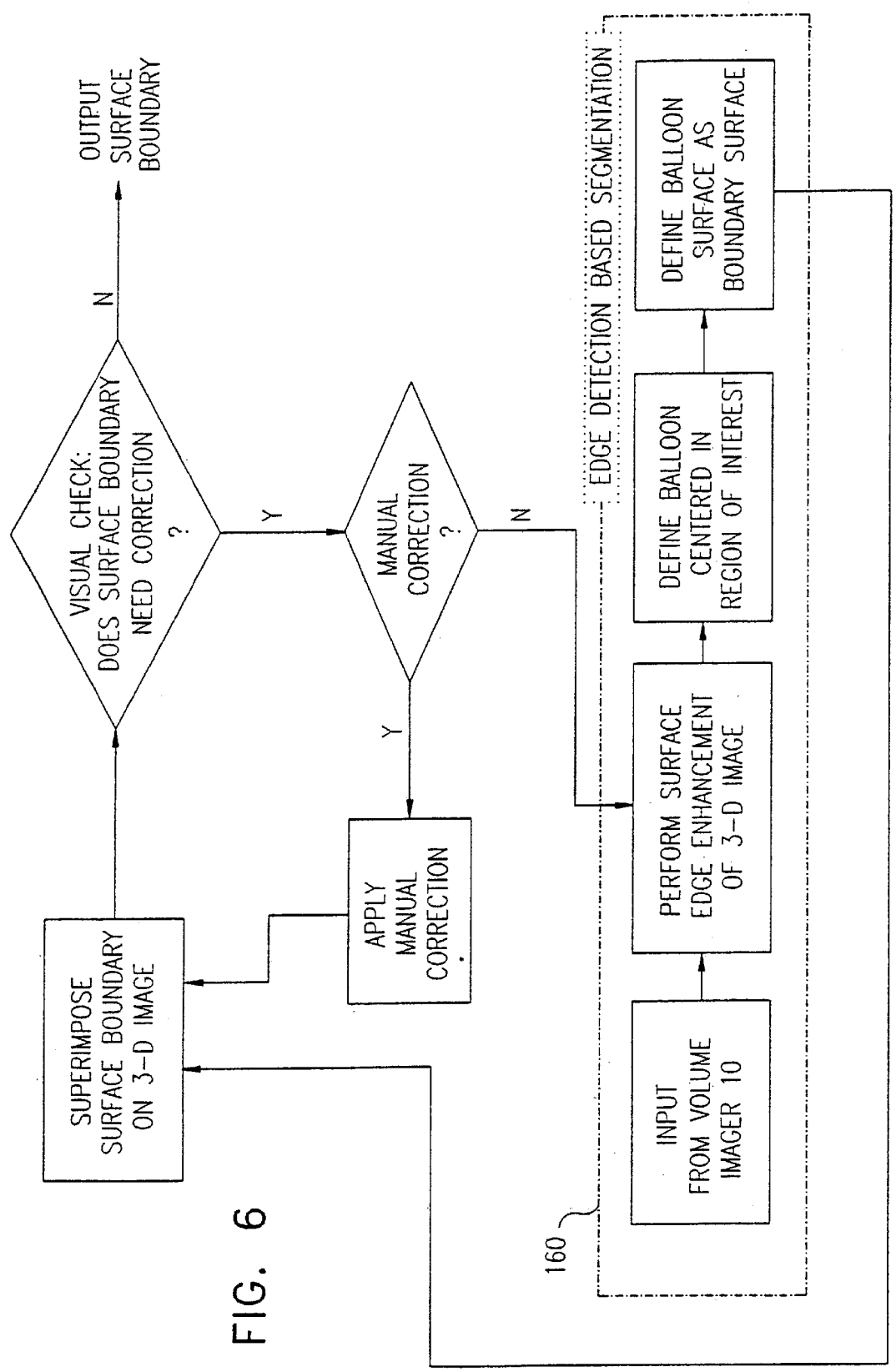
FIG. 6 is a flow chart illustrating 3-D image segmentation step of the operation of FIG. 3A in accordance with a preferred embodiment of the present invention.
Figure 8A:
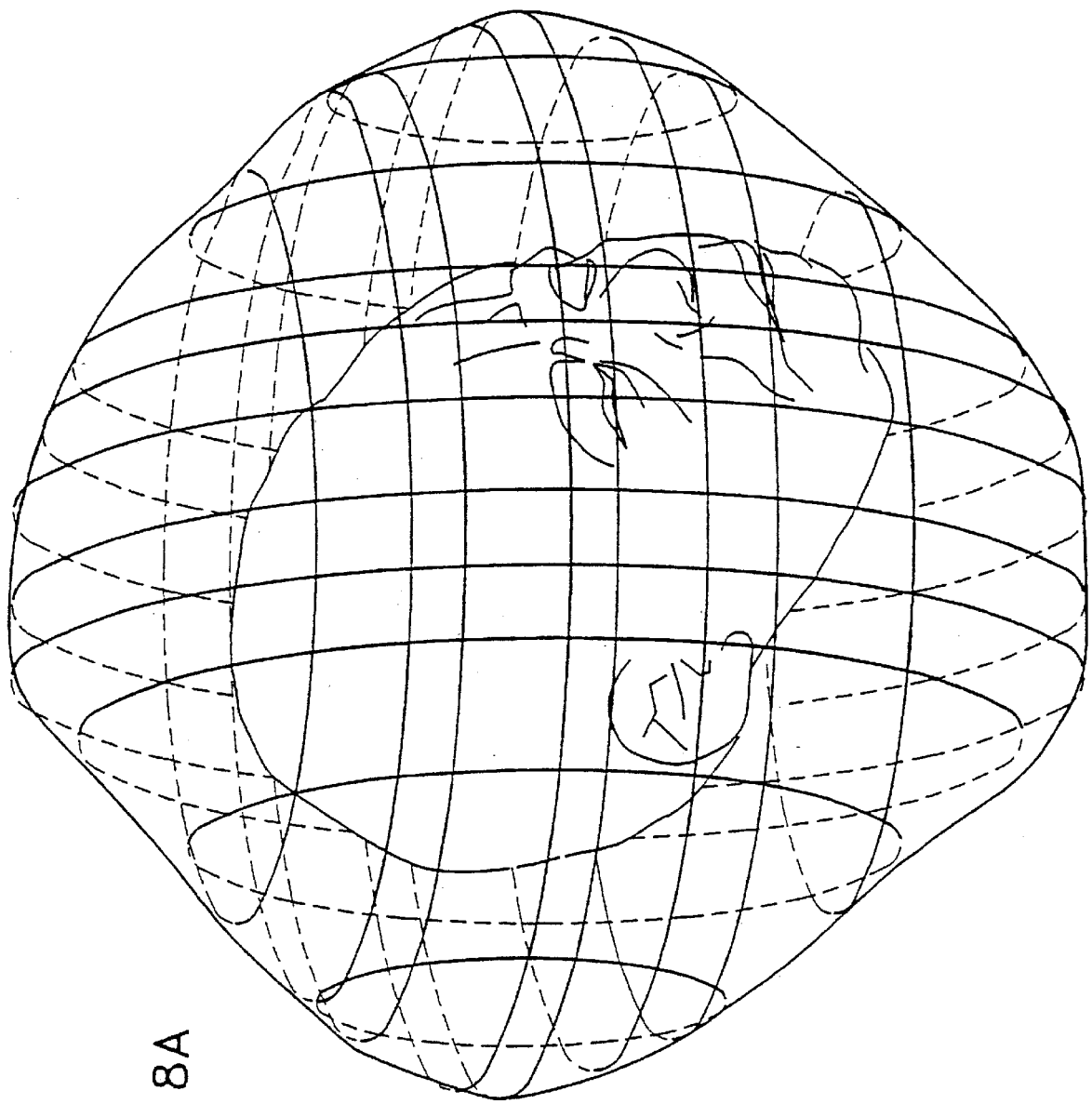
FIGS. 8A, 8B, 8C and 8D are pictorial illustrations showing the progressive shrinking of an imaging balloon about an image of the head of a fetus.
Figure 8B:
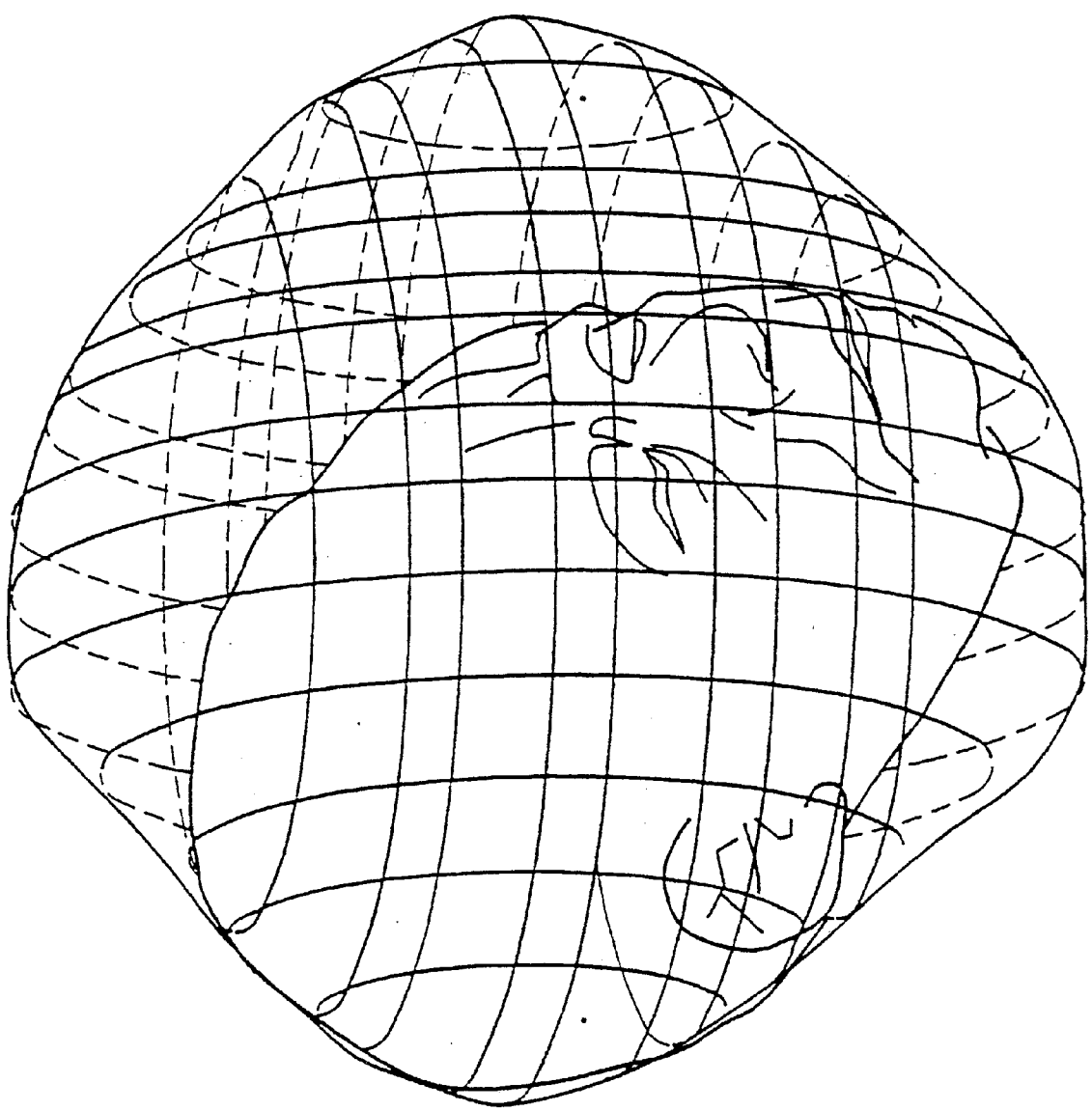
Figure 8C:
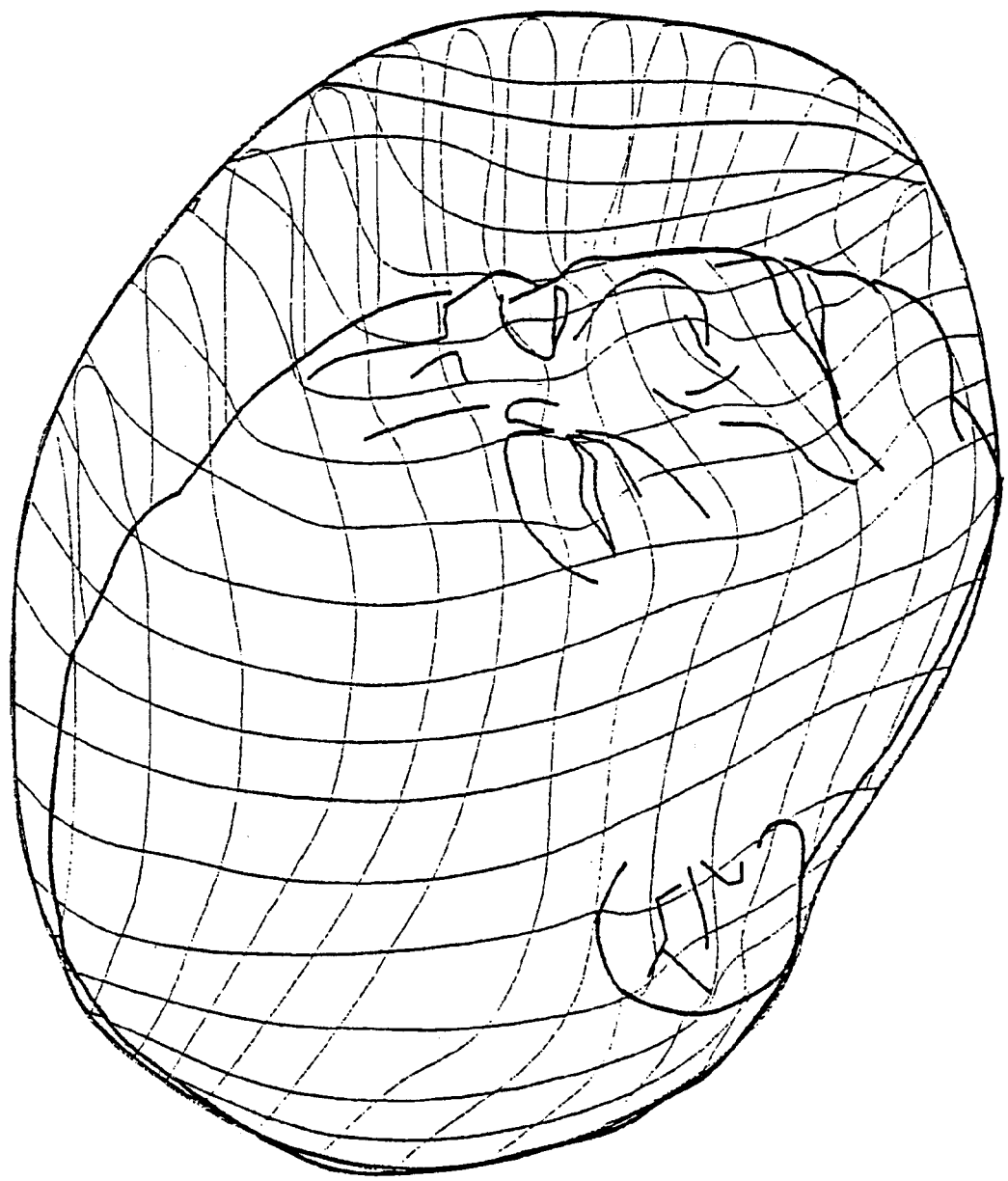
Figure 8D:
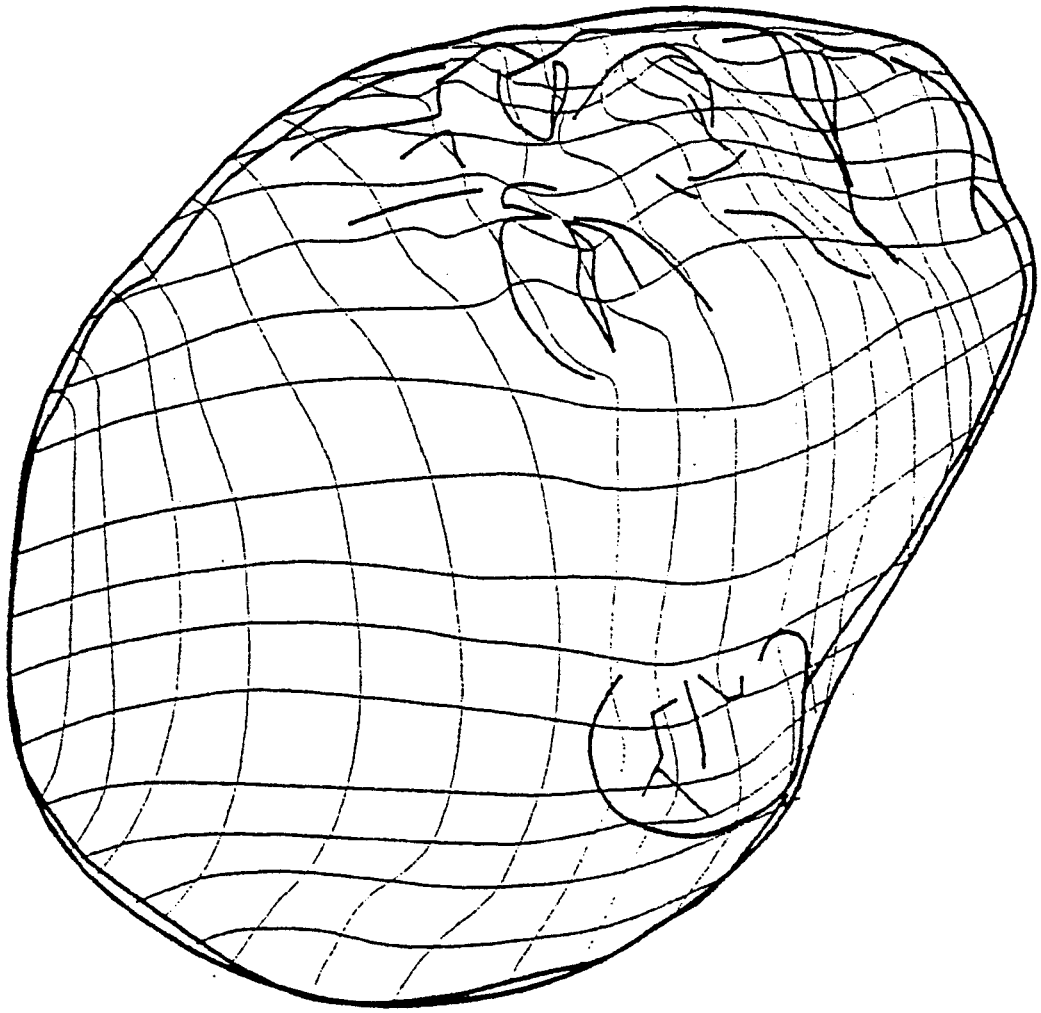

Reference is now made to FIG. 6, which is a flow chart illustrating the 3-D segmentation step of the operation of FIG. 3A in accordance with a preferred embodiment of the present invention.

As seen in FIG. 6, a 3-D image which may have associated therewith initial markings distinguishing between portions of the image which are of interest and portions of the image which it is desired to discard, is subjected to surface edge detection based segmentation 160 which preferably initially performs surface edge enhancement on the received 3-D image.

Following surface edge enhancement, a balloon is defined which is centered on a region of the image which is of interest. The balloon may be defined with the assistance of operator generated markings on the 3-D image, but does not require such markings.

The balloon may be subsequently automatically expanded or shrunk until its boundaries lie on or near enhanced edges of the 3-D image or on operator input markings, which may be supplied in the course of 3-D segmentation and not only prior thereto. The final balloon configuration defines one or more surface boundary. An example of progressive shrinkage of the balloon about a fetal head is illustrated in FIGS. 8A, 8B, 8C and 8D. Shrinkage of the balloon is known from the following prior art publications, the disclosures of which are hereby incorporated by reference:

On Active Contour Models and Balloons, Laurent D. Cohen, CVGIP: IMAGE UNDERSTANDING, Vol. 53, No. 2, March, pp 211–218, 1991;

Finite-Element Methods for Active Contour Models and Balloons for 2-D and 3-D Images, Laurent D. Cohen and Isaac Cohen, IEEE TRANSACTIONS ON PATTERN ANALYSIS AND MACHINE INTELLIGENCE, Vol. 15, No. 11, November, 1993, pp 1131–1147;

Snakes, Active Contours, and Deformable Models http://www.wpi.edu/~dima/ummed/presentation/index.html.

The resultant one or more surface boundary is superimposed on the 3-D image. An operator may carry out a visual confirmation check to satisfy himself that the indicated boundaries are indeed correct. If so, a closed surface boundary superimposed on the 3-D image is output.

Should the operator not be satisfied with the indicated surface boundary or boundaries he can carry out a manual correction or may additionally or alternatively have the boundaries recalculated by edge detection based segmentation 160. Whichever method is chosen, the corrected boundaries are superimposed on the 3-D image and a further visual check is conducted repeatedly until the operator is satisfied with the indicated boundaries.

Reference is now made to FIG. 7, which is a flow chart illustrating a surface edge enhancement step of the operation of FIG. 6 in accordance with a preferred embodiment of the present invention. As seen in FIG. 7, following input of the image from imager 110 (FIG. 1), the volume image is preferably blurred using a 3-D filter, such as a 3-D Gaussian filter. Thereafter, a 3-D median filter is preferably applied to the blurred volume image. The preceding two steps are examples of noise suppression techniques useful in edge enhancement pre-processing.

Following the noise suppression steps described above, a plane enhancement filter is applied to the pre-processed image, thus producing a surface edge enhanced volume image output.

Figure 10:
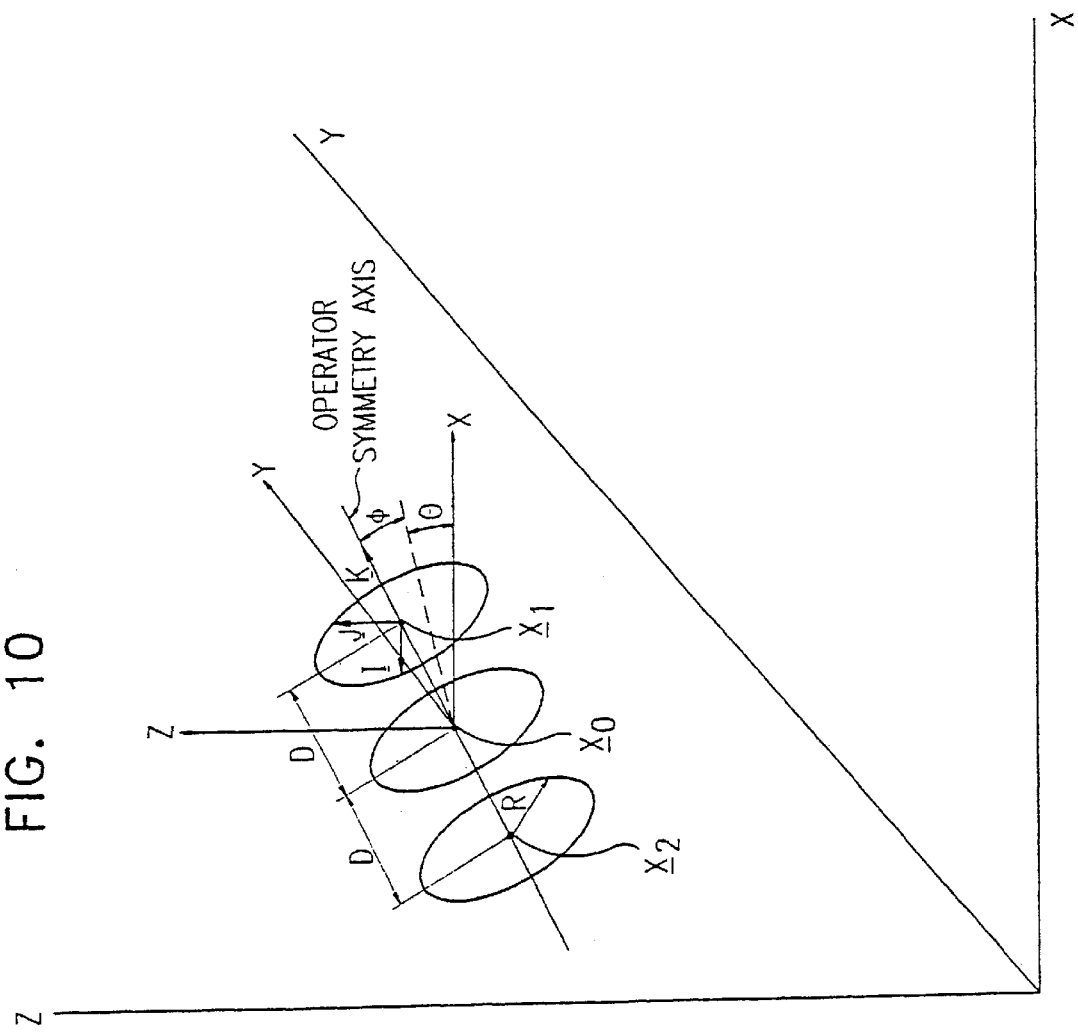
FIG. 10 is an illustration useful in understanding the filtering operation illustrated in FIGS. 9A and 9B.

Reference is now made to FIGS. 9A and 9B which together are a flowchart illustrating a three-dimensional filtering operation performed in accordance with a preferred embodiment of the present invention on an original volume image. Such a filtering operation is preferably employed as part of the step of performing surface edge enhancement of a 3-D image forming part of edge detection based segmentation 160, as shown in FIG. 6 and corresponds to the step in FIG. 7 identified as "APPLY PLANE ENHANCEMENT FILTER". Reference is also made in this context to FIG. 10, which is an illustration useful in understanding the filtering operation illustrated in FIGS. 9A and 9B;

FIGS. 9A and 9B taken together with FIG. 10, describe steps of a filtering operation which is performed on the volume image received from imager 110 (FIG. 1) in accordance with a preferred embodiment of the present invention. The detailed flowchart of FIGS. 9A and 9B describes a plane enhancement operator. The plane enhancement operator is an extension to three dimensions of edge or ridge enhancement operators in 2 dimensions described hereinbelow with reference to FIGS. 13A & 13B as well as FIG. 17.

The plane enhancement operator operates upon a volumetric image and provides a grey-level volumetric image output in which the edges or ridges appear as enhanced surfaces in 3 dimensions. Stated more generally, the plane enhancement operator provides a volumetric image representation of the intensity of the surface edge property at each image voxel. FIG. 10 is an illustration of the plane enhancement operator whose functionality is detailed in FIGS. 9A & 9B. For the sake of conciseness, in view of the detailed nature of the steps of the operation indicated in FIGS. 9A and 9B with reference to FIG. 10, a further textual explanation of these steps is believed to be unnecessary and thus is not provided.

Figure 11:
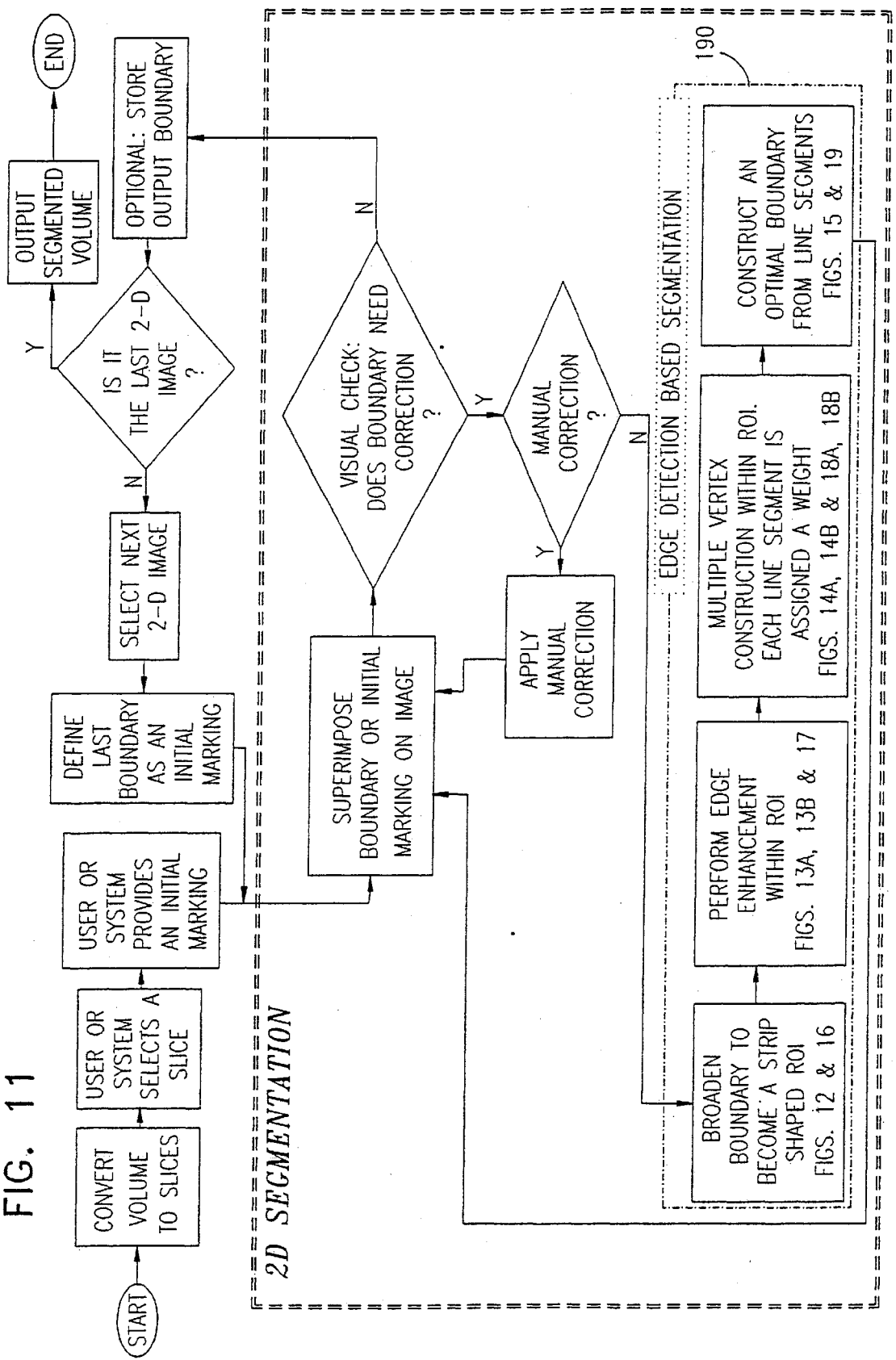
FIG. 11 is a flow chart illustrating 3-D image segmentation step of the operation of FIG. 3A in accordance with a preferred embodiment of the present invention.

Reference is now made to FIG. 11, which is a flow chart illustrating a slice-by-slice image segmentation step of the operation of FIG. 3A in accordance with a preferred embodiment of the present invention. As seen in FIG. 11, a 2-D image, which may be sliced from a volume image, is selected by the system or by an operator and is initially operated on by the segmenter using an operator input which applies initial markings, such as boundary markings, to various portions of the 2-D image to distinguish between portions of the image which are of interest and portions of the image which it is desired to discard.

Thereafter fully or partially computerized 2-D segmentation is carried out using edge detection techniques in accordance with an algorithm which is described hereinbelow. The segmenter provides an output which may be stored while additional 2-D image slices are segmented as described hereinabove.

For each subsequent 2-D image, the output and/or other characteristics of at least one preceding 2-D image are used as initial markings or in any other suitable manner for determining or partially determining the boundary. It is appreciated that the image may include more than one boundary. Once all of the 2-D images have been segmented, a segmentation output is provided to the measurement tool.

The segmentation output defines a closed boundary or boundaries distinguishing portions of the image which are of interest and portions of the image which it is desired to discard.

The 2-D segmentation step shown in FIG. 11 preferably incorporates the following steps:

Initial markings or the preceding boundary are superimposed on the image and a visual check of the boundary may then be carried out. If the boundary appears to need correction and a manual correction is called for, a manual correction is carried out. If, however the boundary does not appear to need correction, it is preferably stored. If the slice being segmented is the last 2-D image slice to be segment in the 3-D image, the volume having the output boundary or boundaries superimposed thereover is output. If the slice being segmented is not the last 2-D slice to be segmented in the 3-D image, a further 2-D slice is selected. The previous boundary is preferably defined as an initial boundary for the further slice.

If, however, the boundary or boundaries are found to need correction and manual correction is selected, a manual correction module applies a manual correction to the boundary or boundaries superimposed on the image. If manual correction is not called for, computerized correction is typically effected by edge detection based segmentation circuitry 190.

Figure 18A:
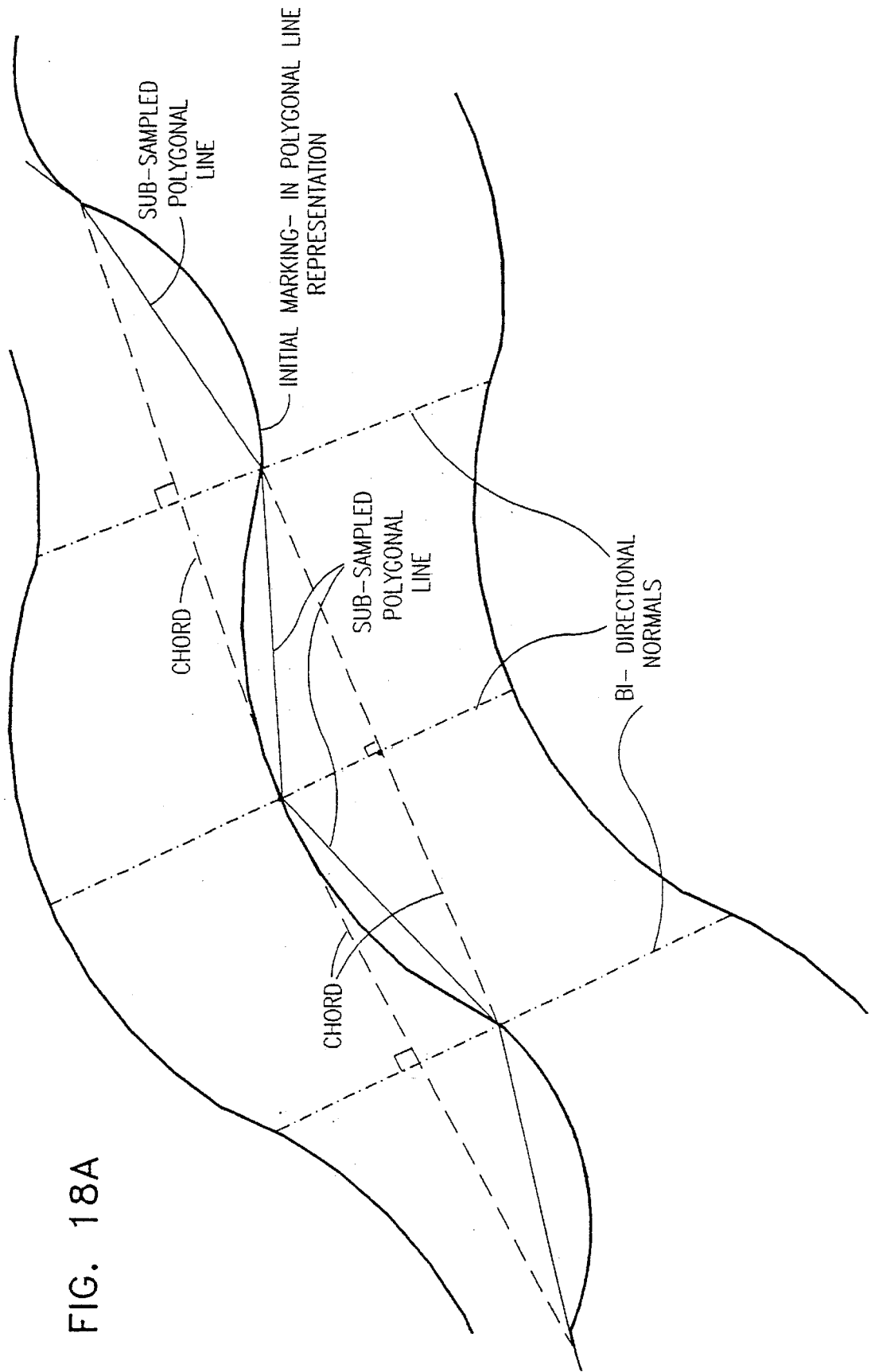
FIGS. 18A and 18B are illustrations useful in understanding the flowchart of FIG. 14.
Figure 18B:
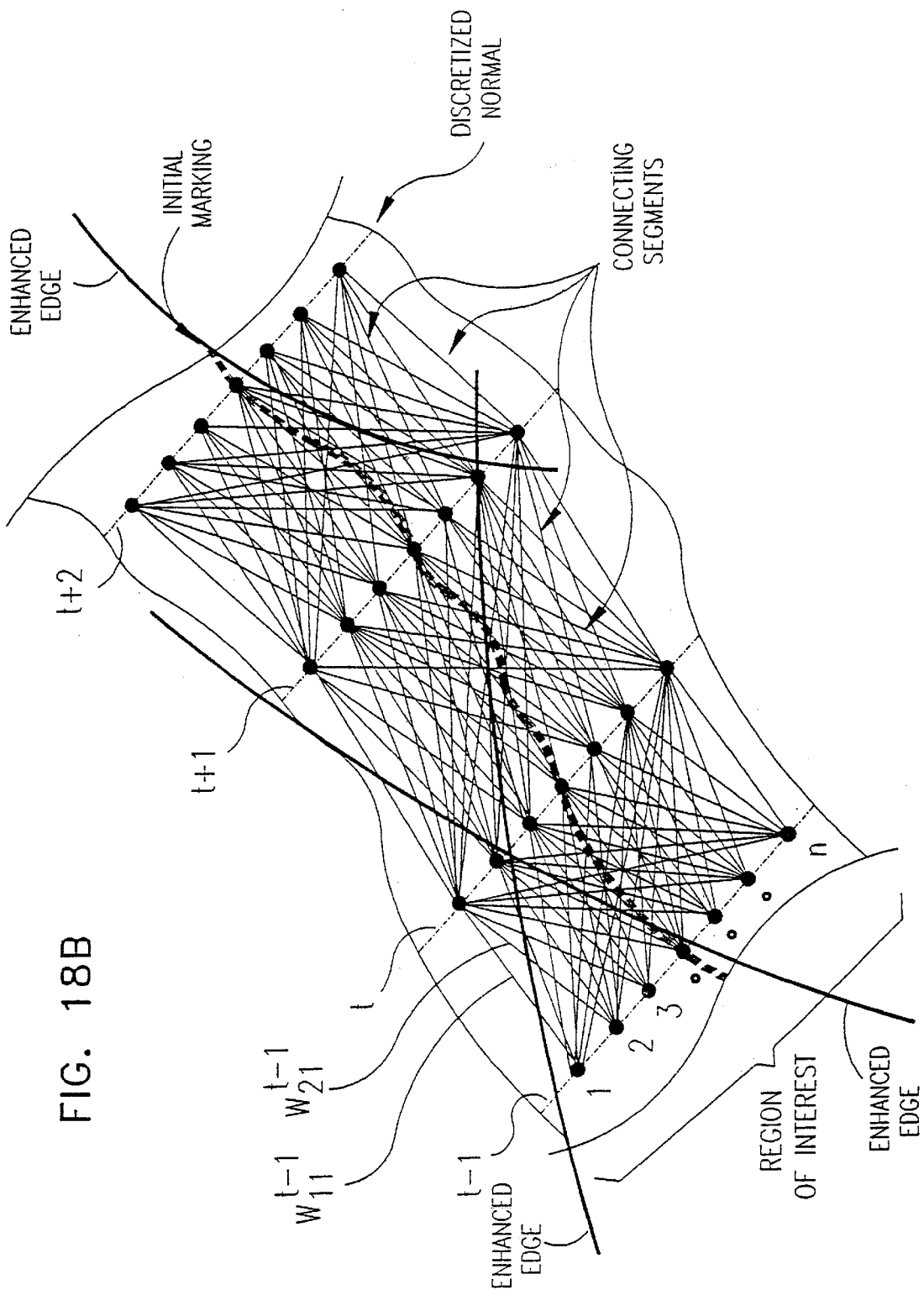

The operation of edge detection based segmentation circuitry 190 may be summarized as follows: The boundary or boundaries initially superimposed on the image are supplied to circuitry 190 separately from the image and are broadened in order to define a strip-shaped region or regions of interest (ROI). Edge enhancement is performed on the image, preferably, but not necessarily, within the ROI. As seen in FIGS. 18A & 18B, referred to hereinbelow, a multiple vertex geometrical construction is provided within the region of interest and includes a multiplicity of vertices interconnected by line segments, wherein each line segment is assigned a weight. As described in greater detail hereinbelow, an optimal boundary is constructed from the line segments. The optimal boundary is then superimposed onto the image.

The foregoing segmentation method continues until it is decided that the boundary on the last 2-D image of the volume does not require correction.

Figure 12:
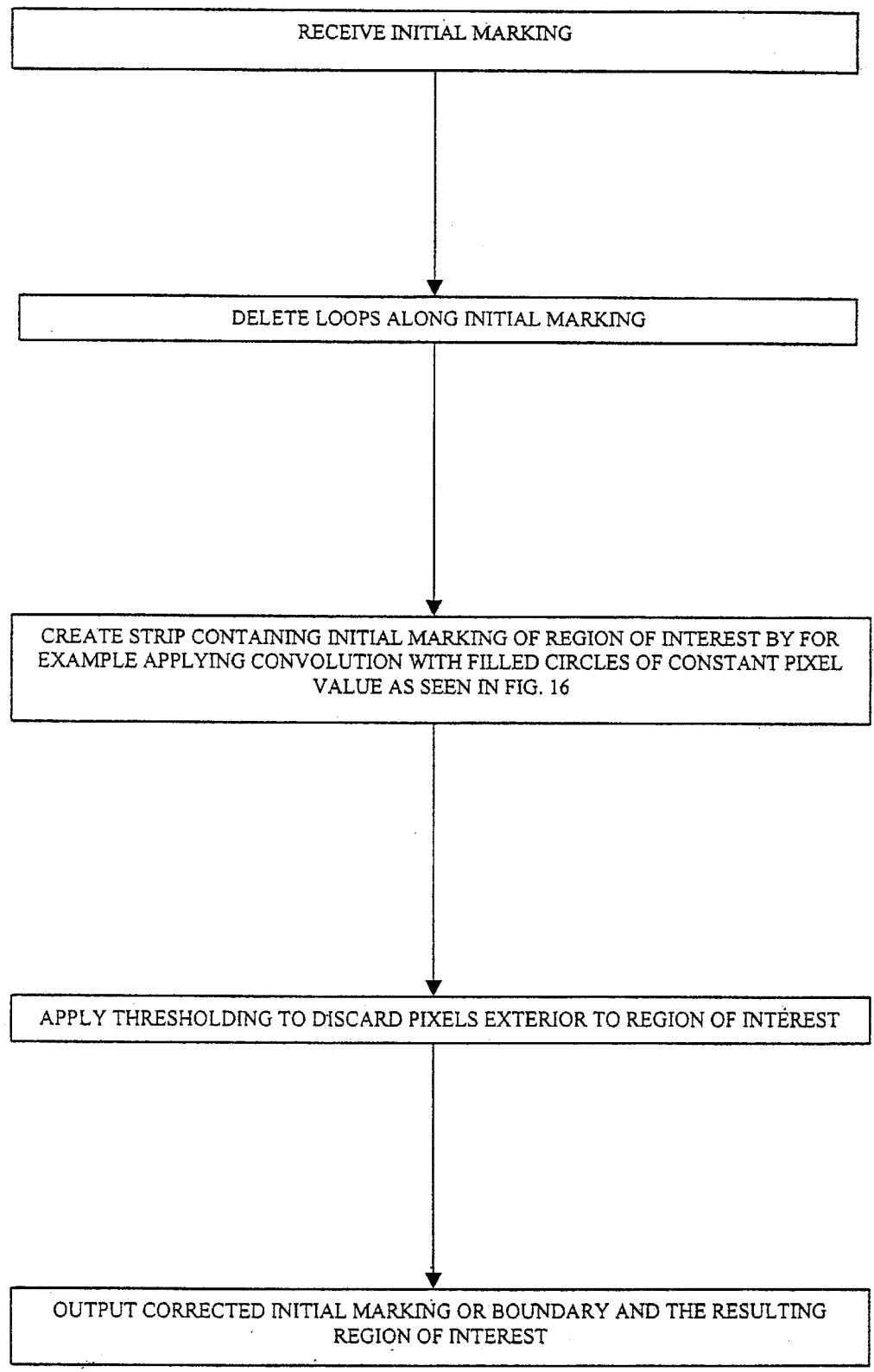
FIG. 12 is a flow chart illustrating a region of interest defining step of the operation of FIG. 11 in accordance with a preferred embodiment of the present invention.
Figure 16:
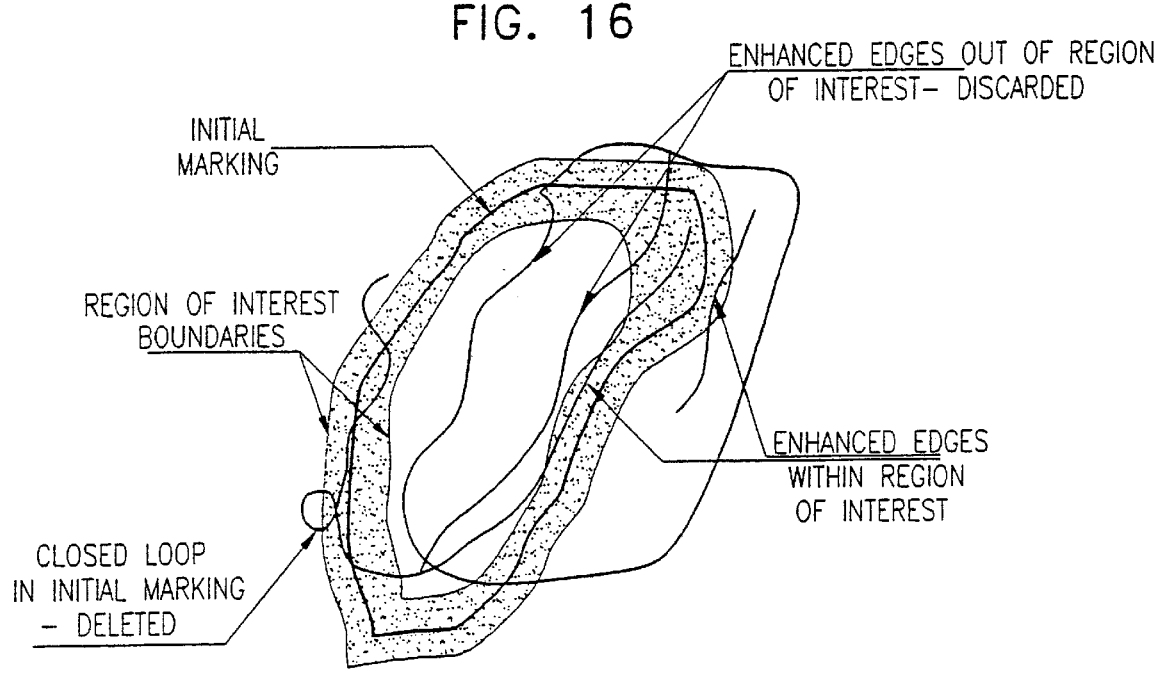
FIG. 16 is an illustration useful in understanding the flowchart of FIG. 12.

Reference is now made to FIG. 12, which is a flow chart illustrating a strip shaped region of interest defining step of the operation of FIG. 11 in accordance with a preferred embodiment of the present invention and to FIG. 16 which shows such a region of interest.

As seen in FIG. 12, the initial marking or boundary is received and any closed loops along the initial marking or boundary are deleted. A strip-shaped region of interest is defined about each initial marking or boundary, for example by employing a convolution having filled circles of constant pixel value as a convolution kernel. The circles need not all have the same diameter. A thresholding function is then applied to discard pixels located exteriorly to the region of interest. The thus-corrected initial marking or boundary is then output together with the strip-shaped region of interest.

Figure 17:
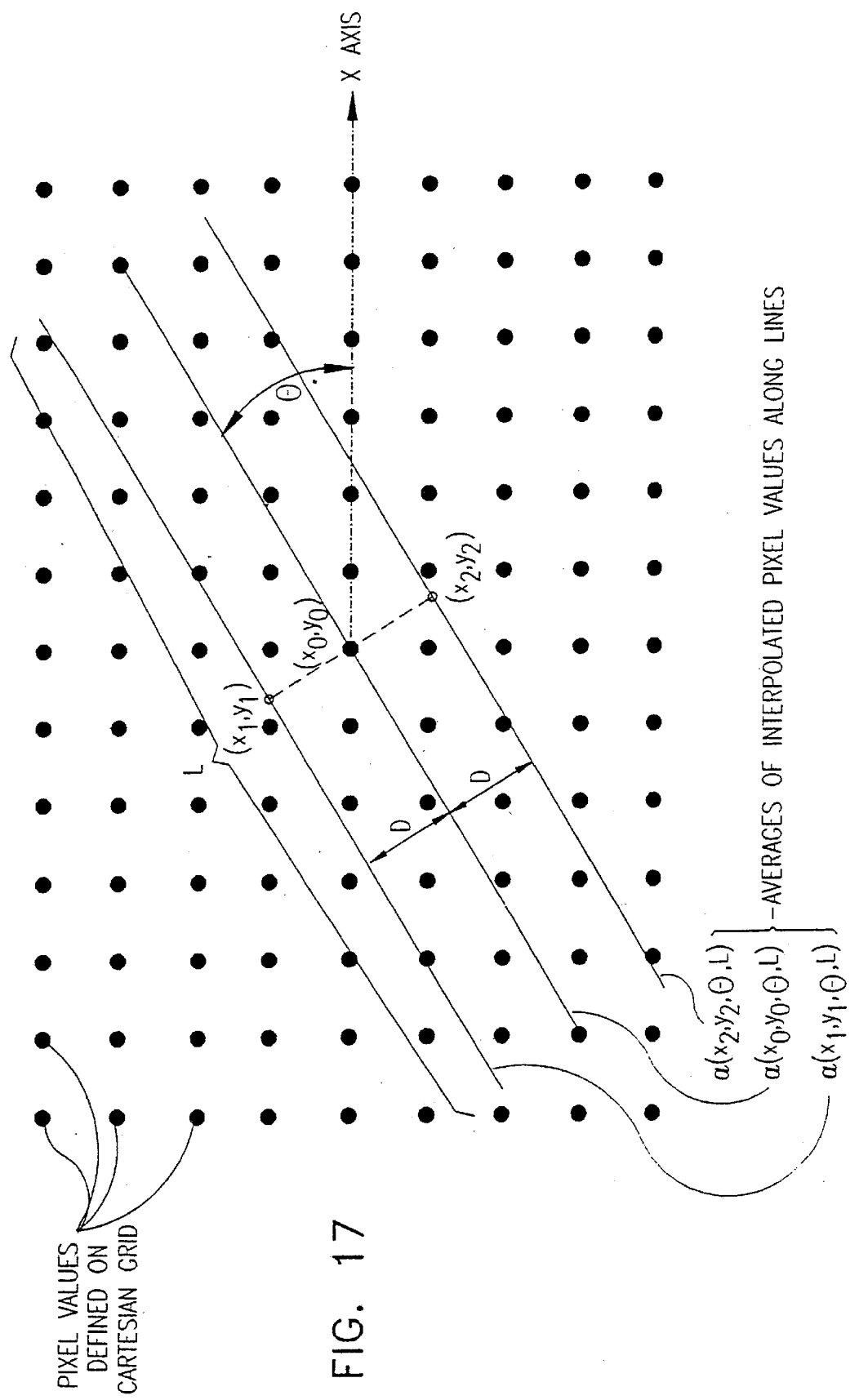
FIG. 17 is an illustration useful in understanding the flowchart of FIGS. 13A and 13B.

Reference is now made to FIGS. 13A and 13B, which together are a flowchart illustrating a two-dimensional edge enhancement filtering operation performed in accordance with a preferred embodiment of the present invention on a slice of the original volume image and to FIG. 17, which is an illustration useful in understanding the flowchart of FIGS. 13A and 13B. It is appreciated that the operation of FIGS. 13A and 13B provides a grey level edge enhanced image. Stated more generally, the operation provides an image representation of the intensity of the edge property at each image pixel.

The operation illustrated in FIGS. 13A, 13B and 17 is carried out at each pixel location in each slice of the volume image and searches for a candidate edge segment at every such pixel location, preferably by searching for the direction of a candidate edge segment. For the sake of conciseness, in view of the detailed nature of the steps of the operation indicated in FIGS. 13A and 13B with reference to FIG. 17, a further textual explanation of these steps is believed to be unnecessary and thus is not provided.

Figure 14A:
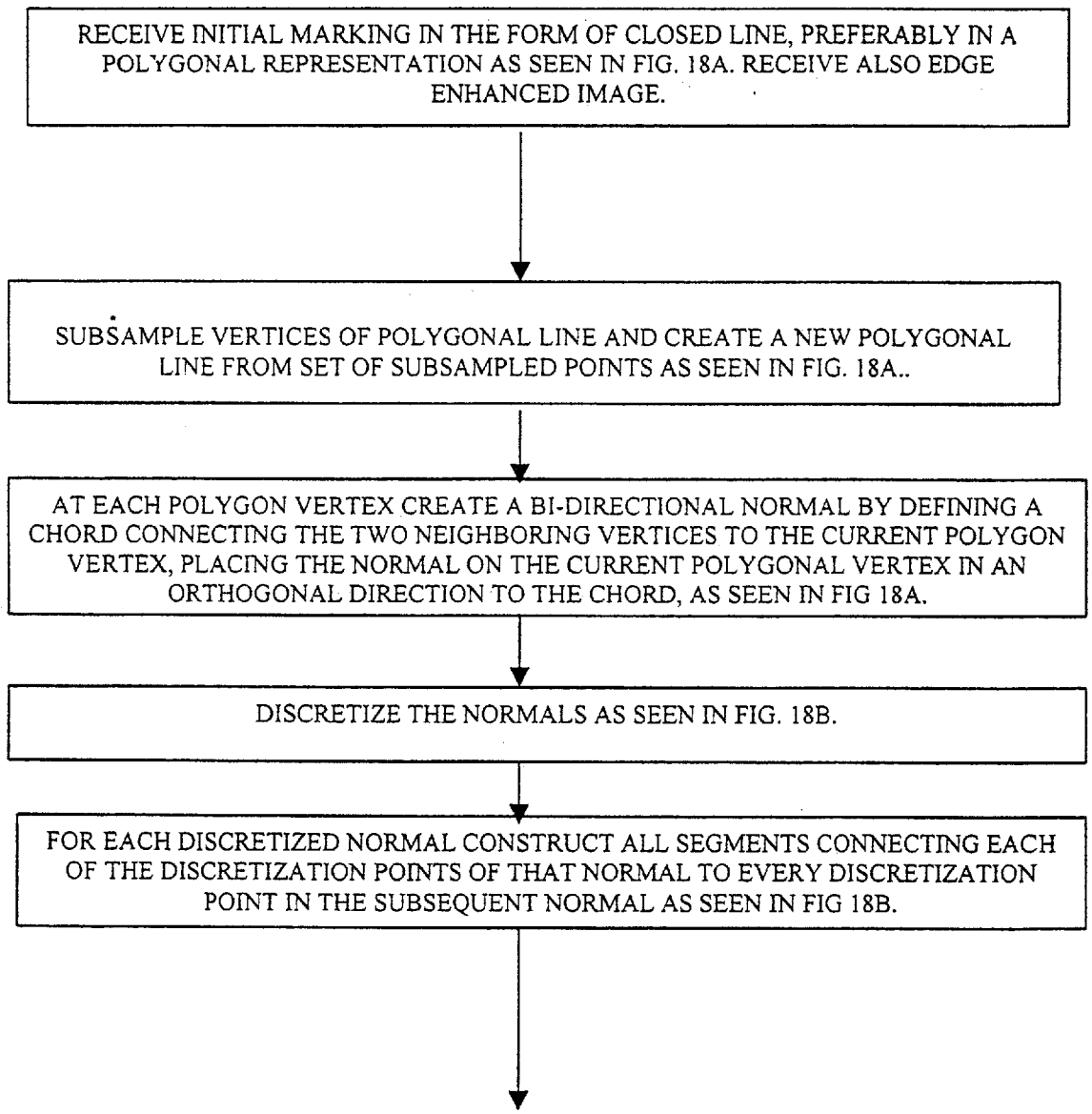

Reference is now made to FIGS. 14A and 14B, which together are a flow chart illustrating one part of an optimal boundary defining step of the operation of FIG. 11 in accordance with a preferred embodiment of the present invention which includes providing a multiple vertex geometrical construction within the region of interest having a multiplicity of vertices interconnected by line segments, wherein each line segment is assigned a weight.

Reference is also made to FIGS. 18A and 18B, which are useful in the understanding of the flow chart of FIGS. 14A & 14B. The functionality of FIGS. 14A & 14B provides information for use in defining a closed boundary within the region of interest. The closed boundary is determined at each point therealong inter alia based on the following characteristics: proximity to an initial marking or a boundary already determined for an adjacent or other slice, the degree of similarity in direction to the initial marking or previously determined boundary and the degree of overlap with the initial marking or previously determined boundary. optionally, not only the configuration of the previously determined boundary for another slice or other slices, but also some or all of the above-listed characteristics of the said slice or slices, may be employed in subsequently determining the boundary for the current slice.

For the sake of conciseness, in view of the detailed nature of the steps of the operation indicated in FIGS. 14A and 14B with reference to FIGS. 18A and 18B, a further textual explanation of these steps is believed to be unnecessary and thus is not provided.

Figure 15:
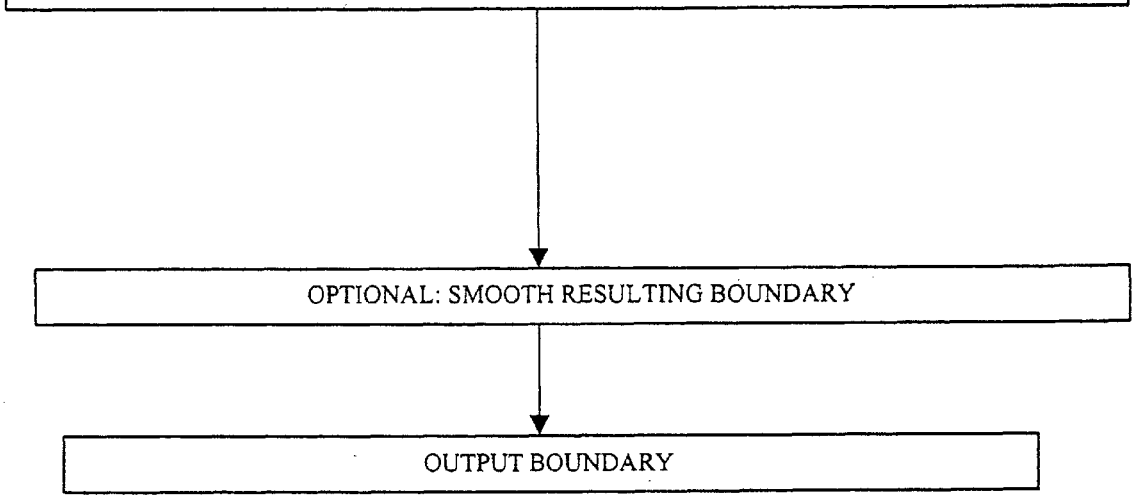
FIG. 15 is a flow chart illustrating another part of the optimal boundary defining step of the operation of FIG. 11 in accordance with a preferred embodiment of the present invention.
Figure 19:
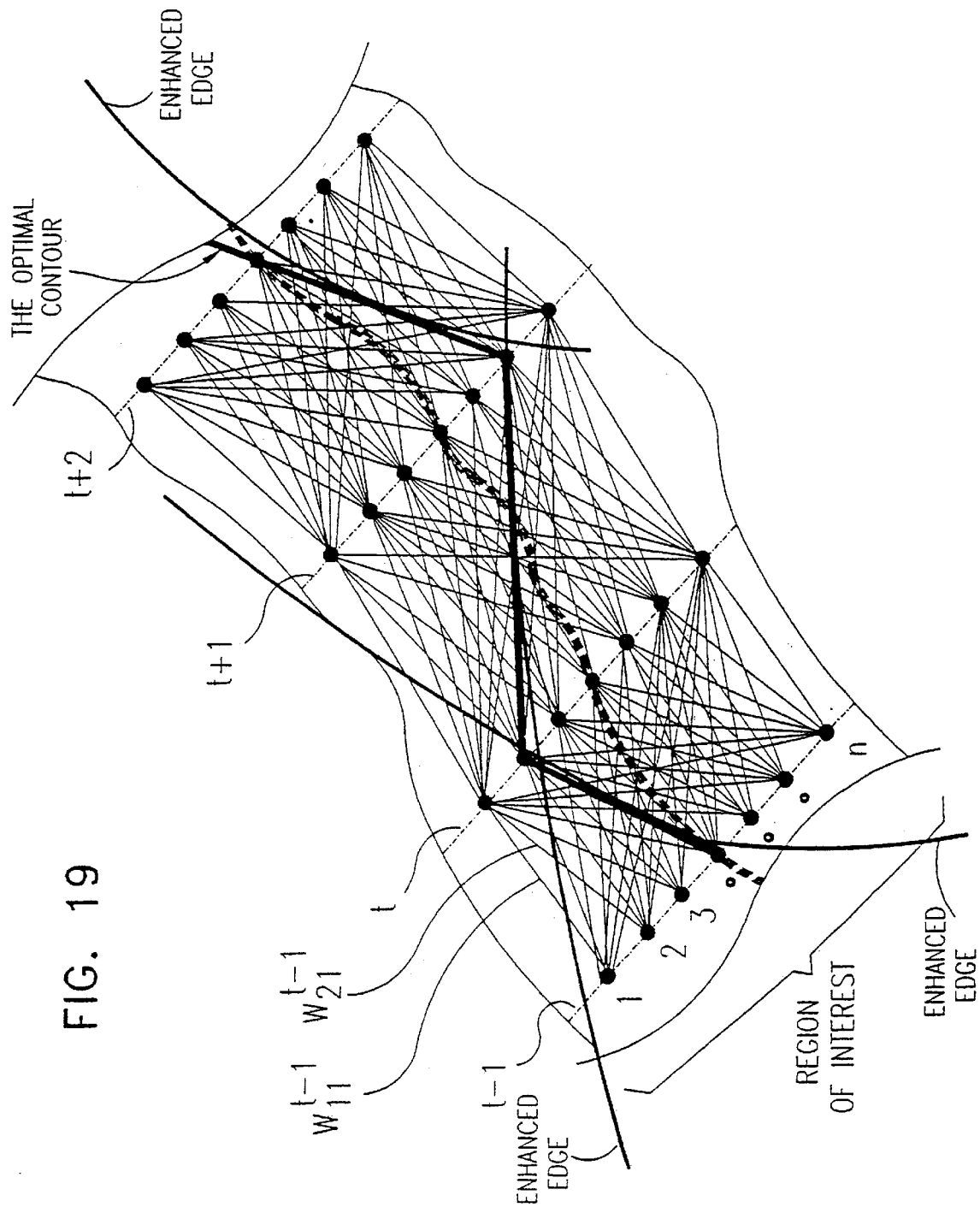
FIG. 19 is an illustration useful in understanding the flowchart of FIG. 15.

Reference is now made to FIG. 15, which is a flow chart illustrating a further part of the optimal boundary defining step of the operation of FIG. 11 in accordance with a preferred embodiment of the present invention which provides an optimal boundary by employing dynamic programming based on the operations described hereinabove with reference to FIGS. 14A, 14B, 18A and 18B. Reference is also made to FIG. 19, which is an illustration useful in understanding the flowchart of FIG. 15.

It will be appreciated by persons skilled in the art that the present invention is not limited to what has been particularly shown and described hereinabove. Rather the scope of the present invention includes both combinations and subcombinations of various elements described hereinabove as well as modifications and variations thereof which would occur to a person skilled in the art upon reading the foregoing description and which are not in the prior art.

What is claimed is:

1. Apparatus for measuring the weight of a fetus in utero comprising:

an ultrasonic imager providing at least one ultrasonic image;

a volume determiner operative to employ said at least one ultrasonic image to provide volume information relating to at least part of the volume of the fetus in utero; and a weight determiner operative to employ said volume information relating to at least part of the volume of the fetus and density information relating to said at least part of the volume of the fetus for providing an output indication representing the weight of said fetus in utero and wherein at least one of said volume determiner and said weight determiner is operative to determine fetal weight from volumes and densities of various body components.

2. Apparatus according to claim 1 and wherein at least one of said imager and said volume determiner operates on a slice-by-slice basis.

3. Apparatus for measuring the weight of a fetus in utero according to claim 1 and wherein said weight determiner comprises a fetal weight calculator receiving inputs relating to at least one of measurement data derived from measurements of a multiplicity of other fetuses, correlations between said measurement data and birth weights, and data from earlier measurements of said same fetus.

4. Apparatus according to claim 1 and wherein said various body components include at least two of the following body components: bones, fat, muscle, skin, soft tissue and fluid.

5. Apparatus for measuring the weight of a fetus in utero comprising:
- an ultrasonic imager providing at least one ultrasonic image;
- a volume determiner operative to employ said at least one ultrasonic image to provide volume information relating to at least part of the volume of the fetus in utero; and
- a weight determiner operative to employ said volume information relating to at least part of the volume of the fetus and density information relating to said at least part of the volume of the fetus for providing an output indication representing the weight of said fetus in utero
- and wherein at least one of said volume determiner and said weight determiner is operative to construct a generally full fetal body volume from incomplete volume information based on known correlation information.

6. Apparatus for measuring the weight of a fetus in utero according to claim 5 and wherein at least one of said volume determiner and said weight determiner is operative to determine fetal weight from volumes and densities of various body components.

7. Apparatus for measuring the weight of a fetus in utero comprising:
- an ultrasonic imager providing at least one ultrasonic image;
- a volume determiner operative to employ said at least one ultrasonic image to provide volume information relating to at least part of the volume of the fetus in utero; and
- a weight determiner operative to employ said volume information relating to at least part of the volume of the fetus and density information relating to said at least part of the volume of the fetus for providing an output indication representing the weight of said fetus in utero
- and wherein said volume determiner comprises computerized image processing based segmenter operative to employ said at least one ultrasonic image to provide size information relating to at least part of the fetus in utero.

8. Apparatus for measuring the weight of a fetus in utero according to claim 7 and wherein said volume determiner also comprises a measurement tool which provides information relating to at least one of overall fetal volume, volumes of body parts of the fetus, areas of various cross sections of the fetus and sizes of various bones and body parts of the fetus.

9. Apparatus for measuring the weight of a fetus in utero according to claim 8 and wherein said measurement tool is operative to measure features of the fetus in at least one selected plane.

10. Apparatus for measuring the weight of a fetus in utero according to claim 9 and wherein said weight determiner comprises a fetal weight calculator receiving inputs relating to at least one of measurement data derived from measurements of a multiplicity of other fetuses, correlations between said measurement data and birth weights, and data from earlier measurements of said same fetus.

11. Apparatus for measuring the weight of a fetus in utero comprising:
- an ultrasonic imager providing at least one ultrasonic image;
- a volume determiner operative to employ said at least one ultrasonic image to provide volume information relating to at least part of the volume of the fetus in utero; and
- a weight determiner operative to employ said volume information relating to at least part of the volume of the fetus and density information relating to said at least part of the volume of the fetus for providing an output indication representing the weight of said fetus in utero
- and wherein said volume determiner comprises a computerized edge detection based segmenter.

12. Apparatus for measuring the weight of a fetus in utero comprising:
- an ultrasonic imager providing at least one ultrasonic image;
- a volume determiner operative to employ said at least one ultrasonic image to provide volume information relating to at least part of the volume of the fetus in utero; and
- a weight determiner operative to employ said volume information relating to at least part of the volume of the fetus and density information relating to said at least part of the volume of the fetus for providing an output indication representing the weight of said fetus in utero
- and wherein said measurement tool is operative to measure features of the fetus in at least one selected plane
- and wherein said volume determiner comprises computerized image processing based segmenter operative to employ said at least one ultrasonic image to provide size information relating to at least part of the fetus in utero.

13. Apparatus for measuring the weight of a fetus in utero comprising:
- an ultrasonic imager providing at least one ultrasonic image;
- a computerized image processing based segmenter operative to employ said at least one ultrasonic image to provide size information relating to at least part of the fetus in utero; and
- a weight determiner operative to employ said size information for providing an output indication representing the weight of said fetus in utero.

14. Apparatus for measuring the weight of a fetus in utero according to claim 13 and wherein at least one of said volume determiner and said weight determiner is operative to construct a generally full fetal body volume from incomplete volume information based on known correlation information.

15. Apparatus for measuring the weight of a fetus in utero according to claim 13 and wherein said volume determiner comprises a computerized edge detection based segmenter.

16. Apparatus according to claim 13 and wherein at least one of said imager and said volume determiner operates on a slice-by-slice basis.

17. Apparatus for measuring the weight of a fetus in utero according to claim 13 and wherein said volume determiner also comprises a measurement tool which provides information relating to at least one of overall fetal volume, volumes of body parts of the fetus, areas of various cross sections of the fetus and sizes of various bones and body parts of the fetus.

18. Apparatus for measuring the weight of a fetus in utero according to claim 13 and wherein said weight determiner comprises a fetal weight calculator receiving inputs relating to at least one of measurement data derived from measurements of a multiplicity of other fetuses, correlations between said measurement data and birth weights, and data from earlier measurements of said same fetus.

19. Apparatus for measuring the weight of a fetus in utero according to claim 13 and wherein said measurement tool is operative to measure features of the fetus in at least one selected plane.

20. Apparatus for measuring the weight of a fetus in utero according to claim 19 and wherein said weight determiner comprises a fetal weight calculator receiving inputs relating to at least one of measurement data derived from measurements of a multiplicity of other fetuses, correlations between said measurement data and birth weights, and data from earlier measurements of said same fetus.

21. Apparatus for measuring the weight of a fetus in utero according to claim 20 and wherein at least one of said volume determiner and said weight determiner is operative to construct a generally full fetal body volume from incomplete volume information based on known correlation information.

22. Apparatus according to claim 20 and wherein at least one of said imager and said volume determiner operates on a slice-by-slice basis.

23. Apparatus according to claim 13 and wherein said segmenter is fully automatic.

24. Apparatus according to claim 13 and wherein said segmenter is semi-automatic.

25. Apparatus according to claim 13 and wherein said segmenter operates substantially in real time.

26. Apparatus according to claim 13 and wherein said segmenter defines geometrical boundaries in at least one slice of said volume by employing previously acquired information relating to at least another slice of said volume.

27. Apparatus according to claim 13 and wherein said segmenter defines geometrical boundaries in at least one slice of said volume by employing previously acquired information relating to at least another slice of said volume.

28. Apparatus according to claim 13 and wherein said segmenter operates in a slice-by-slice manner.

29. Apparatus for measuring the weight of a fetus in utero according to claim 13 and wherein at least one of said volume determiner and said weight determiner is operative to determine fetal weight from volumes and densities of various body components.

30. Apparatus according to claim 29 and wherein said various body components include at least two of the following body components: bones, fat, muscle, skin, soft tissue and fluid.

* * * * *